(12) United States Patent
Evans et al.

(10) Patent No.: US 9,921,173 B2
(45) Date of Patent: Mar. 20, 2018

(54) X-RAY DIFFRACTION IMAGING SYSTEM USING DEBYE RING ENVELOPES

(71) Applicants: The Nottingham Trent University, Nottingham (GB); Cranfield University, Cranfield (GB)

(72) Inventors: Paul Evans, Nottingham (GB); Keith Rogers, Swindon (GB)

(73) Assignees: The Nottingham Trent University, Nottingham (GB); Cranfield University, Cranfield (GB)

( * ) Notice: Subject to any disclaimer, the term of this patent is extended or adjusted under 35 U.S.C. 154(b) by 164 days.

(21) Appl. No.: 14/761,315

(22) PCT Filed: Jan. 2, 2014

(86) PCT No.: PCT/GB2014/050001
§ 371 (c)(1),
(2) Date: Jul. 16, 2015

(87) PCT Pub. No.: WO2014/111684
PCT Pub. Date: Jul. 24, 2014

(65) Prior Publication Data
US 2015/0362443 A1 Dec. 17, 2015

(30) Foreign Application Priority Data
Jan. 17, 2013 (GB) .................................. 1300869.3

(51) Int. Cl.
*G01N 23/20* (2006.01)
*G01N 23/205* (2018.01)
*G01N 23/04* (2018.01)
*H04N 5/232* (2006.01)
*H04N 5/32* (2006.01)

(52) U.S. Cl.
CPC ....... *G01N 23/2055* (2013.01); *G01N 23/046* (2013.01); *G01N 23/20008* (2013.01); *G01N 23/20083* (2013.01); *H04N 5/23293* (2013.01); *H04N 5/32* (2013.01); *G01N 2223/419* (2013.01); *G01N 2223/64* (2013.01)

(58) Field of Classification Search
CPC ........ G01N 23/00; G01N 23/02; G01N 23/04; G01N 23/043; G01N 23/046; G01N 23/20; G01N 23/20083; G01N 23/205; G01N 23/2055; H04N 5/32; H04N 5/232; H04N 5/23293; A61B 6/025; A61B 6/022; G21K 1/06
USPC ...................... 378/21, 41, 70, 71, 73, 88, 90
See application file for complete search history.

(56) References Cited

FOREIGN PATENT DOCUMENTS

WO 2008/149078 A1 12/2008
WO 2011/158047 A1 12/2011

*Primary Examiner* — Jurie Yun
(74) *Attorney, Agent, or Firm* — Jordan IP Law, LLC; Todd A. Vaughn

(57) ABSTRACT

A sample (106) is irradiated with electromagnetic radiation such as X-Rays and diffraction data is sampled at inner and outer caustic rims formed at a sensor surface (108) and defined by a continuum of Debye cones (130, 132) formed by diffraction of the incident radiation. Intensities of the inner and outer rims while translating and rotating the sample are converted using a tomographic technique into X-ray diffraction images and material discrimination is also possible.

17 Claims, 20 Drawing Sheets

X-RAY DIFFRACTION IMAGING SYSTEM USING DEBYE RING ENVELOPES

The present disclosure relates to improvements in sample analysis, and in particular analysis which comprises irradiating a sample with electromagnetic radiation.

The disclosure can relate to any type of electromagnetic radiation but has particular utility for X-rays. Electromagnetic waves having energies in the range of 120 eV up to 1 MeV or beyond may typically be termed as "X-rays".

It is known to image objects using X-rays by measuring X-ray absorption. Typically this involves having an X-ray source and detector with a sample in between them. The primary X-ray beam is directed towards and hits the sample, with some of the X-ray radiation being absorbed, some being scattered and the remainder going on to hit the detector.

X-ray absorption imaging is reasonably effective for imaging the shape of a structure, however reliance on the absorption characteristics of the objects under inspection produces low overall accuracy in terms of material identification. For example dual-energy X-ray imaging exploits the difference in atomic cross section between the photoelectric absorption and the Compton scattering processes inferred by the relative change in magnitude of a high-energy X-ray signal and a low-energy X-ray signal. Consequently an appropriately calibrated X-ray system may be employed to broadly discriminate an inspected object into a limited number of material classes. The discrimination information may be presented to the human observer by colour coding the resultant X-ray images. Thus, for example, security personnel in an airport might review the contents of bags going through an X-ray scanner and can look at the pseudo colours displayed as well as the shape to identify anything suspicious.

Such X-ray absorption techniques can be used in real time and on everyday objects, however such techniques allow only for crude discrimination of materials. Existing absorption techniques are not adequate for distinguishing between materials that have similar chemical signatures, or for detection of objects that have flat shapes. For example, X-ray absorption imaging is unsuitable for the identification of precise material useful to find explosive substances or contraband drugs.

It is also known to solve the structure of a crystal by analysing the scattering of X-rays through a crystal, for example by analysing the diffraction pattern produced. This is known as X-ray crystallography.

A small portion of a primary X-ray beam incident onto a crystal is scattered at measurable angles if its wavelength is similar to the lattice distances (or d-spacing) present in the crystalline material under inspection. For ideal, polycrystalline materials interrogated by pencil beams, the photon scatter follows a cone distribution, with the source of the scattering at the cone apex. These "Debye cones" form circular patterns when they intersect a flat detector normally. For the purposes of the present disclosure, these patterns can be approximated to and considered as circles for a relative inclination of the detector with respect to the primary ray or interrogating tubular beam ray under consideration even though in practice they are elliptical. These circles have a common centre coincident with that of the incident beam position on the detector. The angular distribution of the scattered intensity is unique to each different crystal structure and thus can be used to identify a material and determine characteristics such as lattice dimensions, crystallite size and percentage crystallinity. The key relationship between the lattice spacing (d), and the scatter angle ($\theta$) is embodied within the well known Bragg condition: $\lambda = 2d \sin \theta$ (where $\lambda$ is the X-ray wavelength).

X-ray crystallography allows for the structure of a large number of molecules of different materials including inorganic compounds to be determined. Ordinarily this is done with single crystals though it is possible to obtain significant information from powdered material or from thin films. This technique allows a large amount of information about materials to be determined. However, even where powders rather than single crystals are used it is frequently a requirement to prepare a custom made small sample which is then bombarded with X-rays perhaps over many hours to provide adequate detection and subsequent analysis of the diffraction pattern.

Conventional powder diffractometers utilise detectors to scan and measure a portion of the resultant diffraction pattern. This angular dispersive technique usually employs monochromatic X-rays. Data collection and analysis have been based mainly on one-dimensional (1D) intensity profiles obtained with scanning point detectors or linear detectors. The linear detector is often referred to in the field as a position sensitive detector or PSD. The use of 2D image sensors (array or area detectors) may be used to speed up the collection of data in comparison to point or line detectors.

Some of the commonly used X-ray scattering techniques are: single crystal diffraction (SCD), X-ray powder diffraction (XRPD), high-resolution X-ray diffraction (HRXRD), X-ray reflectometry (XRR) and small angle X-ray scattering (SAXS). In general diffractometers are laboratory instruments which are designed for off-line inspection requiring relatively long periods of data collection from carefully prepared samples, because the amount of radiation that is scattered is relatively low and therefore long integration periods are required in order to accumulate a sufficient amount of signal for accurate measurement. For this and other reasons X-ray crystallography can be a very effective technique in laboratories for slow analysis but would not generally be suitable for everyday objects or for use in "real time" or "on-line" inspection applications.

Bragg diffraction may occur whenever the wavelength of incident radiation is of a similar magnitude to the lattice spacing of a crystal under analysis, and so crystallography techniques are not limited to X-rays. Particles such as neutrons or electrons can be used if at the correct energy; as well as other electromagnetic radiation.

An alternative technique is disclosed in WO 2008/149078, which is incorporated herein by reference. The output of an X-ray source is configured, for example by an annular collimator, to form a curtain of X-ray radiation, which can be tubular and/or cone shaped for example. A detector is placed at a position where the Debye cones of X-ray radiation emitted from a sample overlap to form regions of increased intensity, which leads to increased sensitivity and better material discrimination. The technique can be performed over a much shorter time period than that of standard X-ray crystallography.

A further improvement is also disclosed in WO 2011/158047, which is incorporated herein by reference. This disclosure builds on that of WO 2008/149078 by combining high spatial resolution X-ray absorption data (or imagery) with coherently scattered or diffracted X-rays. When a diffraction signal corresponding to a feature of interest is identified, known positional coordinates from the absorption data can be matched to the scattering data, meaning that one can identify the scattering angle. This therefore provides unique XRD signatures for crystalline materials such as:

manufactured materials such as metals, alloys, ceramics, cements; minerals such as rocks, salts, soils; Organic materials such as drugs, chemicals, sugars, proteins, etc; and has applications in security imaging, forensics—drug detection; non-destructive testing & evaluation (NDT&E); production (quality assurance, process control); instrumentation; and medical diagnostics.

However, despite these improvements and innovative uses of diffraction data for generation of signatures, there remain fundamental problems of low speed and low signal to noise ratio still associated with diffraction based imaging.

According to a first aspect of the disclosure there is provided a method of sample analysis comprising irradiating a sample with electromagnetic radiation and sampling radiation diffracted by the sample, said sampling being performed from a variety of different perspective views, and combining data from two or more of said different perspective views to obtain information about the sample.

Optionally, the irradiating electromagnetic radiation comprises at least one tubular beam the shape of which may be a right circular cylinder or a cone.

The tubular beam may be formed by passing the electromagnetic radiation rays through a collimator that comprises an electromagnetic radiation blocking body portion and one or more electromagnetic radiation transmitting apertures, the shape of which defines the shape of the tubular beam or beams.

Optionally, the collection of the scattering data is carried out at caustic rims formed by the overlap of a continuum of Debye rings around a path defined by the primary interrogating beam.

Optionally, an image or a series of images are prepared for viewing.

Optionally, geometrically matched perspective views are produced from a series of different rims along one radial direction.

Optionally, a series of geometrically identical perspective views are produced as determined by a single generator ray.

Optionally, matched views are registered with respect to one another. This enables one to combine and enhance signal deficiencies or reveal complete shape information, enhanced detail or varying material properties that may be present in the individual images.

Optionally, a composite image is formed by tomosynthesis employing a set of rim-derived X and Y raster scanned perspective images which produce a focal plane image convolved with an apparent annular aperture.

Optionally, said apparent annular aperture has a zero effective aperture at a rim.

Optionally, the tomosynthesis provides z height information for the focal pane image to enable two theta diffraction angles to be calculated automatically.

Optionally, the spatial origin of one or more diffraction peaks corresponding to focal plane features is used to identify material properties.

Optionally, the inter-rim focal plane imagery is deconvolved to recover useful signal.

Optionally, voxels in a sample are interrogated around a circular path to reveal material properties. Points along said circular path optionally correspond to different radial directions.

Optionally, spatial information is established via a movie sequence showing image features being translated around a circular path as a function of their relative position with respect to a convergence or datum plane.

Optionally, spatial information is established via rotation of the object(s) under inspection, arranged to conserve the direction of parallax along one axis.

Optionally, a binocular stereoscopic image sequence is displayed by maintaining the direction of parallax in the visual display along the horizontal display axes but in opposite directions for the left and right perspective view sequences.

Optionally, spatial information is established via a sequence or stack of focal plane images, produced by tomosynthesis, being displayed as a 'stepwise' movie along a z-axis.

Optionally, the method comprises solving for the diffraction angle for a known relative position with respect to an associated rim, measured parallax, and separation between generator rays for two different radial directions.

Optionally, depth information is identified along radial paths that are independent of the scattering angle.

Optionally, tomography or laminography is carried out on the basis of said identified depth information.

Optionally, images of extended objects directly attributable to individual diffraction lines are produced and combined with other diffraction line views to provide material identification and/or characterisation.

Optionally, said material identification and/or characterisation comprises accounting for a sample's preferred orientation.

Optionally, said material identification and/or characterisation comprises accounting for a sample's grain size.

Optionally, captured perspective images are relayed in a movie sequence of perspective images, which exhibit rotating features, in planes parallel to sensor surface, as a function of their relative depth (Z axis) in a visual display.

Optionally, perspective images produced at different scattering angles are mapped together to provide colour encoding.

Optionally, said colour encoding is implemented via a corresponding pixel positions input to a lookup table.

Optionally, the method comprises irradiating the sample with broadband or white electromagnetic radiation; and performing the sampling at different energy resolutions.

Optionally, the electromagnetic radiation comprises excited K-alpha and/or K-beta characteristic radiation produced by the source.

According to a second aspect of the disclosure there is provided a sample analysis apparatus comprising an electromagnetic radiation source, a detector for collecting electromagnetic radiation scattering data, and a processor for sampling said scattering data according to the methods described above.

According to a third aspect of the disclosure there is provided a computer program product comprising instructions that, when executed by a computer, enable the computer to sample said scattering data according to the methods described above.

The computer program product may comprise computer readable code embodied on a computer readable recording medium. The computer readable recording medium may be any device storing or suitable for storing data in a form that can be read by a computer system, such as for example read-only memory (ROM), random-access memory (RAM), CD-ROMs, magnetic tapes, floppy disks, optical data storage devices, and carrier waves (such as data transmission through packet switched networks such as the Internet, or other networks). The computer readable recording medium can also be distributed over network coupled computer systems so that the computer readable code is stored and executed in a distributed fashion. Also, the development of functional programs, codes, and code segments for accomplishing the present invention will be apparent to those skilled in the art to which the present disclosure pertains.

The present disclosure will now be described, by way of example only, with reference to the accompanying drawings, in which.

Figure 1:
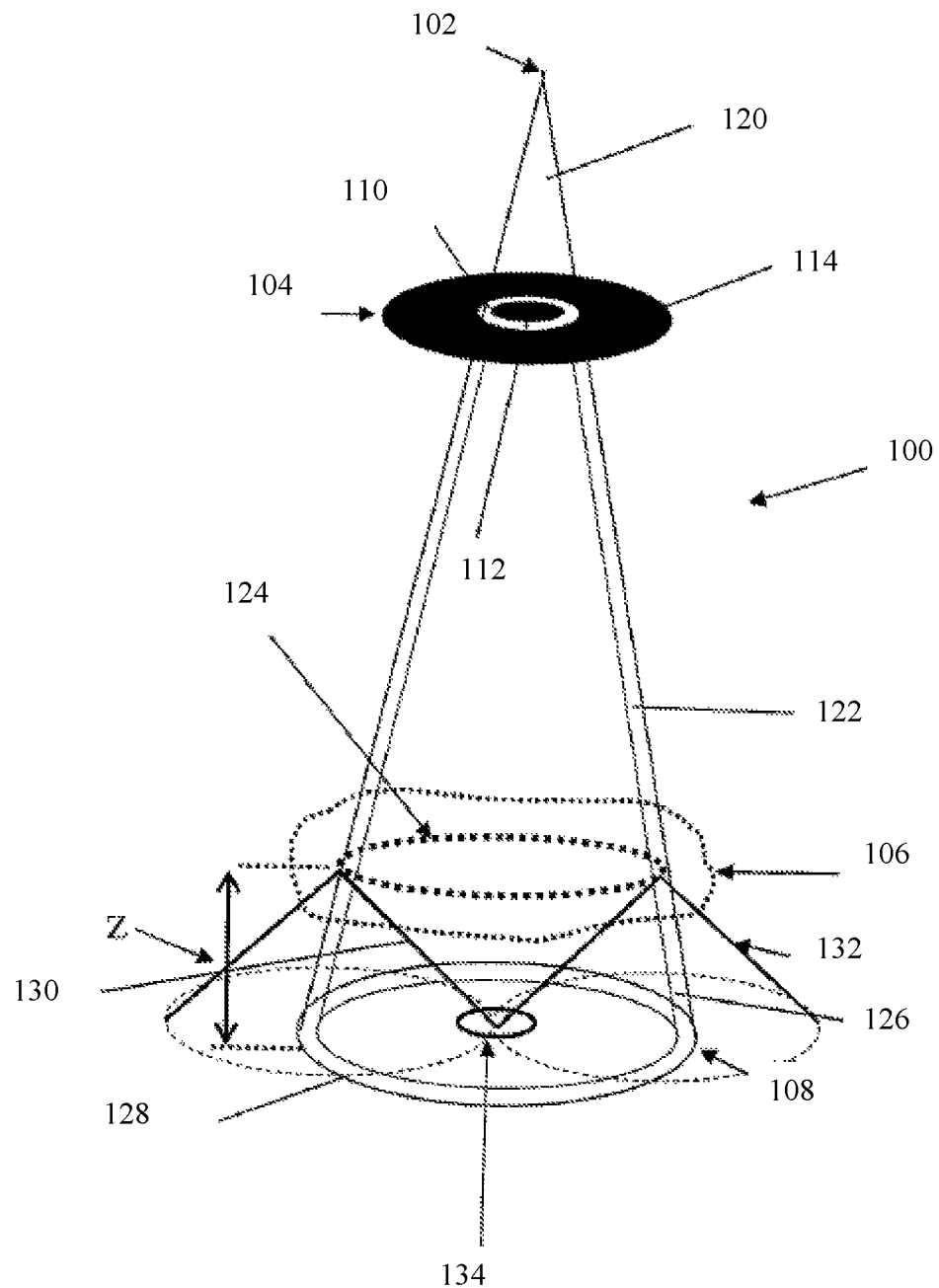
FIG. 1 shows an X-ray scatter gathering apparatus.

FIG. 1 shows an example of an X-ray scatter gathering apparatus 100. The apparatus 100 is suitable for carrying out X-ray crystallography, that is, to gather scattering data. The apparatus 100 comprises an X-ray source 102, a collimator 104, a target object 106, and a detection surface 108 which includes a detector or sensor.

The collimator 104 is a ring collimator in this example, but could be of a different shape if desired. Different shaped collimators may be chosen depending on the particular application area. The collimator 104 is made from a conventional material that might typically be used for collimating X-rays, such as tungsten or steel, which can also support a layer of lead if required. Any material can be used so long as it can significantly block the path of X-rays. The ring collimator 104 comprises an annular aperture 110 between disc 112 and annulus 114. All three of the annulus 114, annular aperture 110 and disc 112 have the same centre point. The disc 112 may be held in its position relative to the annulus 114 by any appropriate means such as being attached via thin wire or by being held in place using electromagnets. Annulus 114 does not need to be circular, rather it needs simply to block the primary beam. A target object 106 is the target from which the apparatus 100 is designed to detect diffracted X-rays. It may comprise a material suspected to be a polycrystalline material and which it is wished to identify. The target object can be of numerous forms but in the example depicted in FIG. 1 it is a plate like object.

The detection surface 108 may comprise a physical surface or it can be the name given to a plane of a hypothetical surface with no physical surface present. Somewhere on the surface 108 (or alternatively along the plane) is a sensor, which can be located at the centre of surface 108 directly in line with the X-ray source and the centre of the ring collimator 104.

The X ray source 102 may be a point source, a line source or a ring source. FIG. 1 illustrates the example of a point source. In theory a point source of X-rays is an isotropic radiator but a practical X-ray source produces a solid angle of X-rays (120) which is aimed towards and therefore incident on the collimator 104. The disc 112 and annulus 114 are made of attenuating material so that they block the majority of these X-rays (120). However, some X-rays do go through the annular aperture 110 and results in the production of a pattern of X rays, which is a conical curtain of X-rays 122 in the example of a ring collimator being used. The cross section of the conical curtain 122 will be a narrow annulus of X-rays, that is the X-rays are present in the shape of a band between a first cone and a second cone which can be imagined to be positioned at a point slightly higher than the first cone. A further possibility, depending on the size of the source 102, is that the cones share the same primary axis and apex position but have different opening angles.

The conical curtain 122 hits the target object 106. Since the target object is substantially planar the conical curtain 122 hits the object 106 in a circular target path 124. Some of these X-rays will be scattered by the lattice of the target object 106 by Bragg diffraction and some absorbed, but much of the primary X-ray radiation will continue. There is a substantially continuous X-ray curtain 126 which then hits the detection surface 108 a distance Z from the target object 106, forming an annulus of primary X-rays 128 at that surface 108.

Because the target object 106 contains a material with a frequently occurring repeat interatomic distance (e.g. for polycrystalline materials a "d-spacing") there is X-ray diffraction causing a scatter of the photons in a conical distribution. These are known as "Debye cones" and they are generated from every point along the circular specimen path 124 so long as a repeating structural component is present. Two such Debye cones are marked in FIG. 1 as 130 and 132. It has been found that a "hotspot" 134 can be generated in the centre of the detection surface 108 provided the distance Z is set correctly.

For a particular polycrystalline material that needs to be identified, the d-spacing and therefore the scattering angle can be calculated so that for a given ring collimator 104 and distance between collimator and sample, the correct distance Z can be calculated where the Debye cones will have the same diameter as the target path 124 in the plane 108 of the sensor, so that a signal of large intensity is generated at the "hotspot" 134. The distance can be fine tuned in practice by moving any of the target object 106, collimator 104 or detection surface 108 so that the maximum radiation intensity is found. The apparatus 100 can be used for an unspecified polycrystalline material. The target object 106, collimator 104 or detection surface 108 can be linearly moved whilst still in line with each other until the detector picks up the large reading of intensity at the hotspot 134. The distances between two or more of the ring collimator 104, detection surface 108 and target object 106 can be measured allowing the angle of scatter of the Debye cones and therefore the d-spacing to be calculated. The material can then be identified on the basis of the calculated d-spacing, as the association of particular d-spacings with particular materials is well established.

It is possible to use excited K-alpha line(s) produced by the source as the incident primary beam. This approach could be combined with (balanced) filtration or monochromator crystals (at the source or the detector), or the use of energy resolving detectors to provide a monochromising effect for the incident signal. This may help reduce noise produced by background incoherent signals generated by Compton scattering that might in some cases otherwise swamp the coherent signal.

If Bremsstrahlung (unfiltered incident spectrum) is present then additional Compton scatter will be produced at the sample and incident upon the detector. An energy resolving detector can be employed to reject (or discriminate) most of this Compton scatter signal. For example, if we were detecting a 60 keV caustic produced by a sample (but the incident radiation was not well filtered and had a long tail of higher energy radiation) then Compton from this tail could produce a "floodlight" effect, e.g. organics can produce a strong Compton signal. Therefore, the rejection of the higher energy "floodlight" could help the detection of coherent signals at 60 keV. Here we ignore the small Compton shifts (in wavelength) around 60 keV to 100 keV for small solid angles at the detector.

FIG. 1 shows two example Debye cones 130 and 132 and their associated Debye rings as formed on an image plane that is perpendicular to the illustrated Z axis. This plane will be referred to as the X-Y plane, being spanned by an X axis and a Y axis. Only two rings are illustrated in FIG. 1 for the purposes of illustration, however, there will in fact be a continuum of Debye rings centred around a path 128 defined by the primary radiation beam after passing through the object 106. This path (as defined by the primary beam) will in practice be an annulus but for the purposes of the present disclosure can be represented by an idealised line; and further, it is herein approximated as a circular line for the purposes of illustration even though in practice it will be annular.

Figure 2:
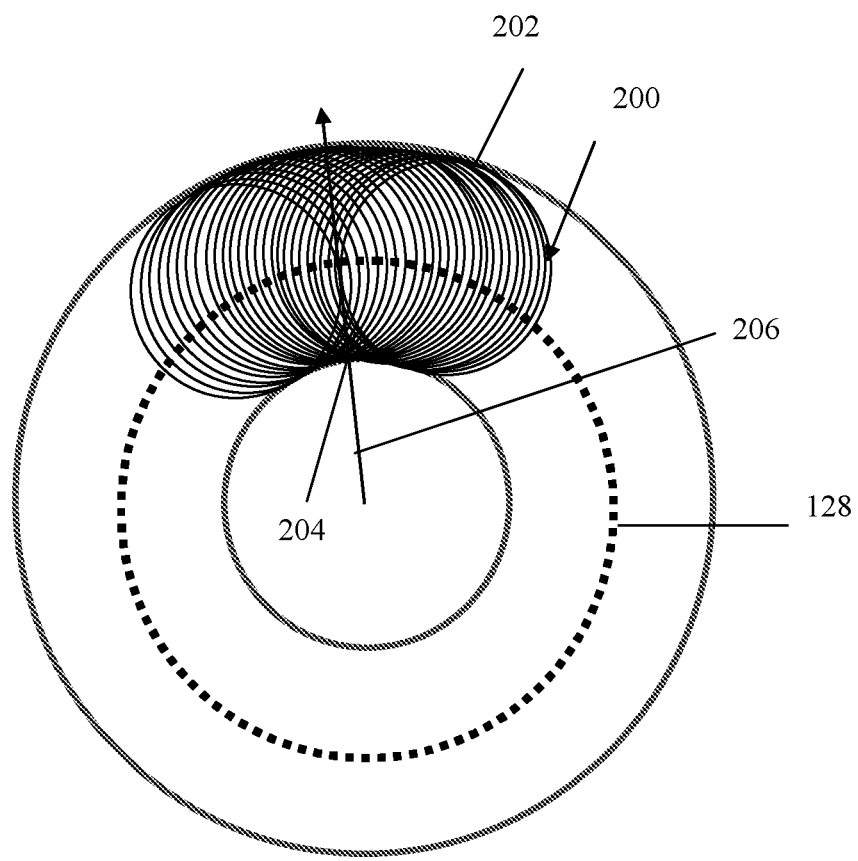
FIG. 2 shows the formation of caustic patterns by "Debye rings" formed at a detection surface of an X-ray scatter gathering apparatus, at a point in a region along a primary axis in which the caustic rims are convergent towards a "hotspot" at which the Debye rings overlap with a maximum intensity.

FIG. 2 now shows a plan view of example Debye rings, which may be derived from an apparatus of the type shown in FIG. 1, or from an equivalent apparatus. The Debye rings of FIG. 2 are of a different size from those shown in the example of FIG. 1. Again, a continuum of Debye rings will be formed but FIG. 2 shows selected rings from the continuum for the purposes of illustration.

Debye rings 200 are each centred around the primary radiation beam 128. As illustrated by the figure, the rings form caustic patterns comprising bright rims around an outer path 202 and an inner path 204. A "caustic pattern" refers to an area of bright illumination, such as a rim. A caustic is a natural focussing into stable lines with a variety of topological features. The rims are characterised according to their geometric properties. An "outer" rim (when considering a single scattering angle or Debye cone) has a form encompassing an "inner" rim. In the example illustrated in FIGS. 1 and 2, an outer rim is radially spaced from an inner rim. There are two different types of inner rim that may be formed, namely; a "closing rim" or an "opening rim".

Before describing the formation and characteristics of rims in more detail it is helpful to define radial direction 206 through the rims and the footprint of the primary X-ray beam in the (x, y) plane. This direction is measured from the centre point of the path defined by the primary radiation beam 128. This directional information may also be recorded within a calibrated three dimensional coordinate system that identifies the location and orientation of the X-ray source and sensor and collimation slit as well as the spatial distribution of the primary X-ray beam.

The size of the Debye rings will depend upon the scattering angle of the diffraction (which depends upon the type of material under test) and the position of the sample plane (Z height as illustrated in FIG. 1). Each Debye cone is concentric about a primary X-ray, which is referred to as a 'generator ray'. Debye cone rays that are incident along the same radial direction as their generator ray contribute to the formation of a rim. A continuum of such rays arising from around a circular specimen path form a relatively high intensity tubular diffraction beam that converges to a hotspot, as illustrated in FIGS. 3 and 4.

Figure 3:
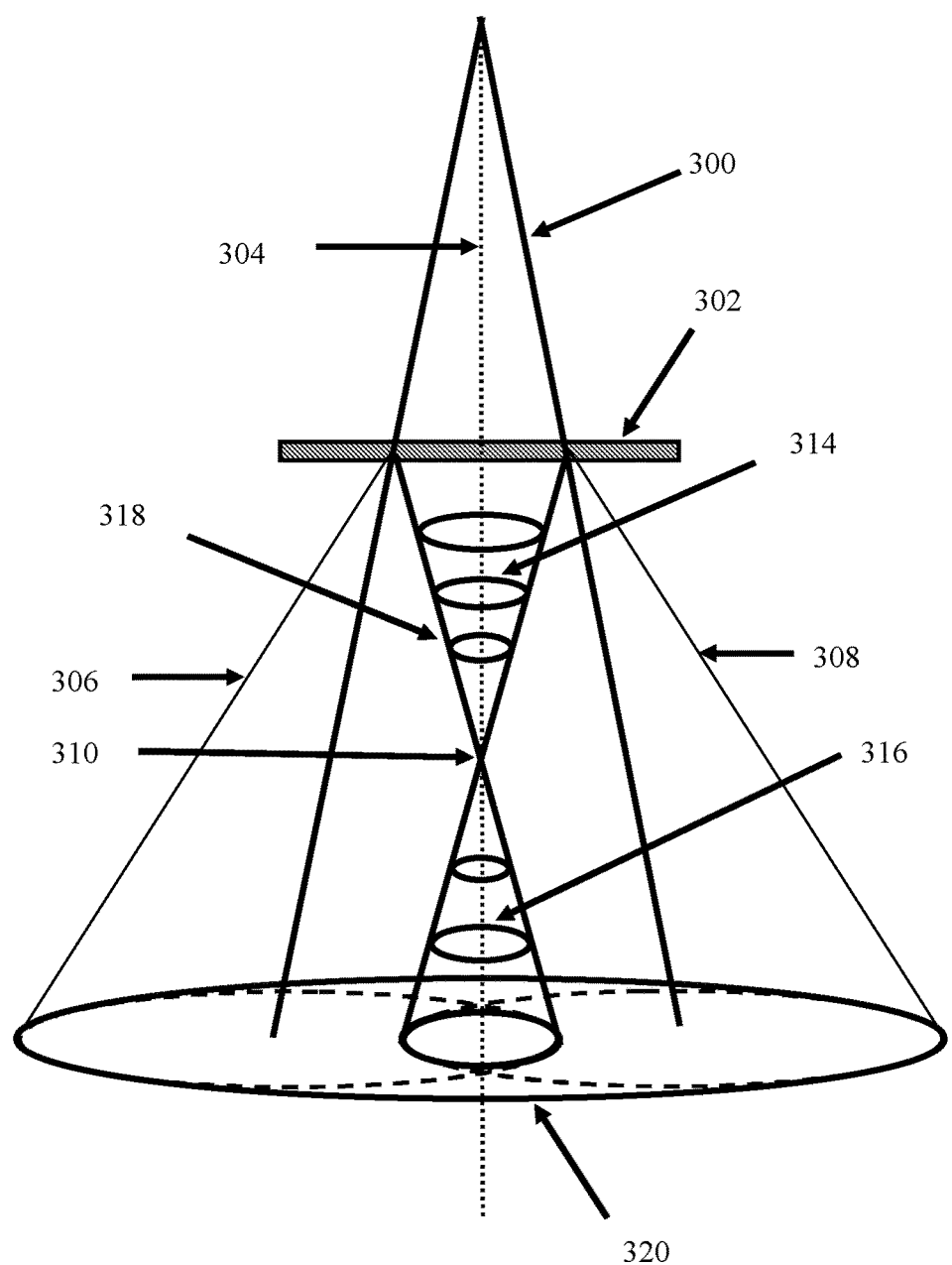
FIG. 3 shows aspects of the formation of caustic rims by a continuum of Debye rings, for an X-ray scatter gathering apparatus operating in transmission mode.
Figure 4:
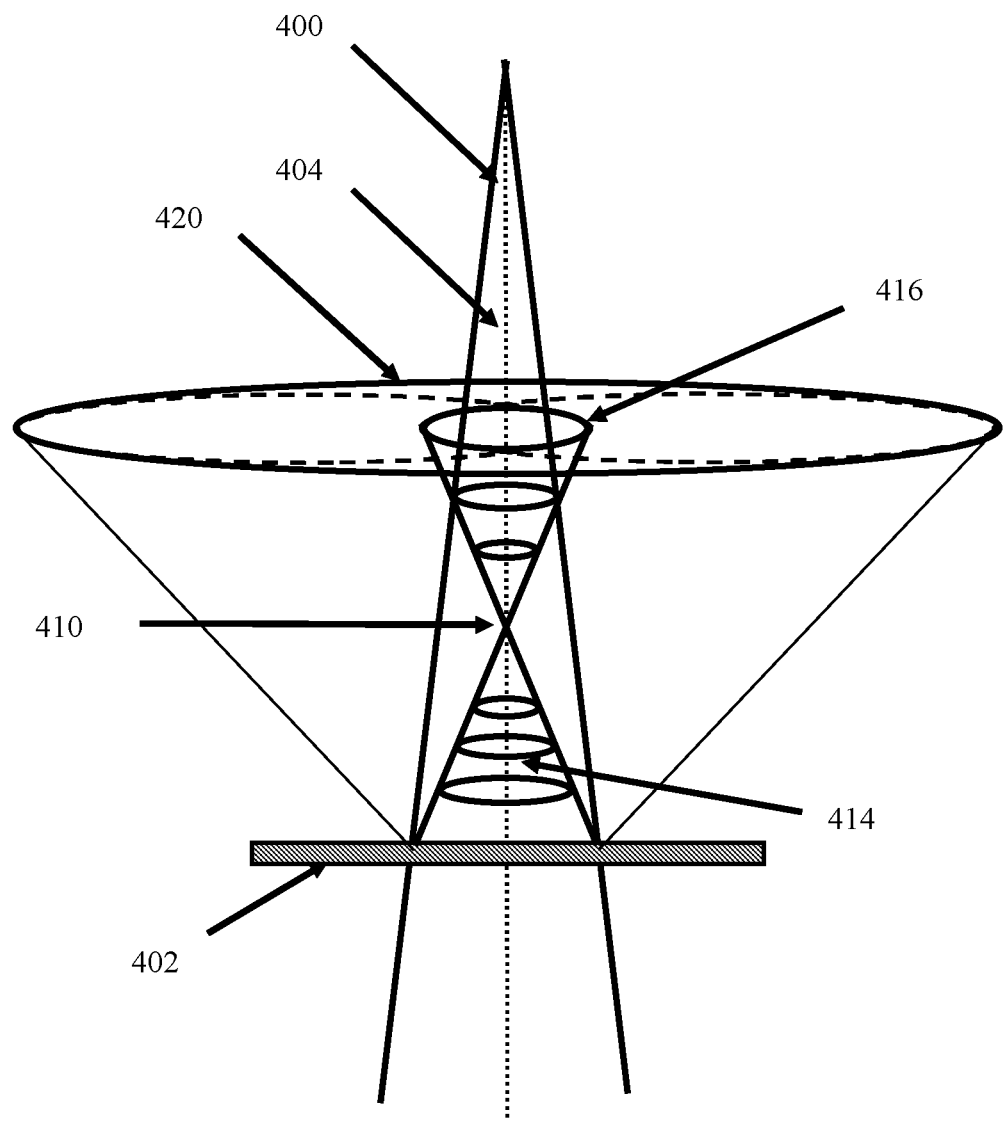
FIG. 4 shows aspects of the formation of caustic rims by a continuum of Debye rings, for an X-ray scatter gathering apparatus operating in an example of a back reflection mode.

FIG. 3 illustrates a transmission diffraction mode. As before, a tubular primary beam 300 is incident upon a sample 302 having a generally planar surface normal to the primary axis 304 of the primary beam 300 and forming Debye rings 306, 308 which overlap at a "hotspot" 310 and are incident (together with the transmitted primary beam) on a detection surface. That is, an inner rim will be a "closing" rim or an "opening" rim depending on the relevant z-axis position, for a given source and sample arrangement. It will be appreciated that the illustrated Debye rings 306, 308 are in fact only two from a continuum of Debye rings around a circular path that are recorded by a planar sensor normal to the primary axis 304. The continuum of the Debye rings around a circular path forms a relatively high intensity convergent tubular beam, illustrated at 318.

Now, the detection surface at which the planar sensor may be positioned can be at any chosen z-height (where a given z-position defines a position along the primary axis 304 which defines the distance by which the detector is spaced from the sample). An outer rim 320 as recorded by a planar sensor normal to the primary axis at one example z-position is shown.

Example inner rims for various different z-positions are illustrated in FIG. 3, with the illustrated ellipses of the figure representing perspective views of the circular rims that are produced in the x-y plane. The inner rims can be classified as "closing" rims if they converge towards the symmetry axis 304 for increasing z-axis positions (in a direction away from the sample and towards the detector), and can be classified as "opening" rims if they diverge away from the symmetry axis 304 for increasing z-axis positions (in a direction away from the sample and towards the detector). FIG. 3 shows three examples of closing rims 314 (sections through a convergent tubular diffraction beam) as would be detected at different detection surface z-positions by a planar sensor normal to the primary axis 304; and three examples of opening rims 316 as would be detected at different detection surface z-positions by a planar sensor normal to the primary axis 304.

FIG. 4 illustrates a back reflection mode. A tubular primary beam 400 with primary axis 404 is incident upon a sample 402. Note that the position and shape of the backscatter detection surface should not block the path of the primary beam 400 or modify its designed operational spectral content or intensity.

An outer rim 420 is shown, as recorded by a planar sensor normal to the primary axis at one example z-position. By placing a detection surface between the sample 402 and the hotspot position 410 the convergent beam produces closing rims positioned within the area bounded by an outer rim, three examples of which are shown at 414. When a detection surface is placed at a z-position beyond the hotspot position 410 the divergent beam produces opening rims, three examples of which are shown at 416.

In both FIGS. 3 and 4, when the detector surface is positioned beyond the hotspot position on its 'divergent' side then the hotspot appears as a 'source' of X-rays.

Figure 5:
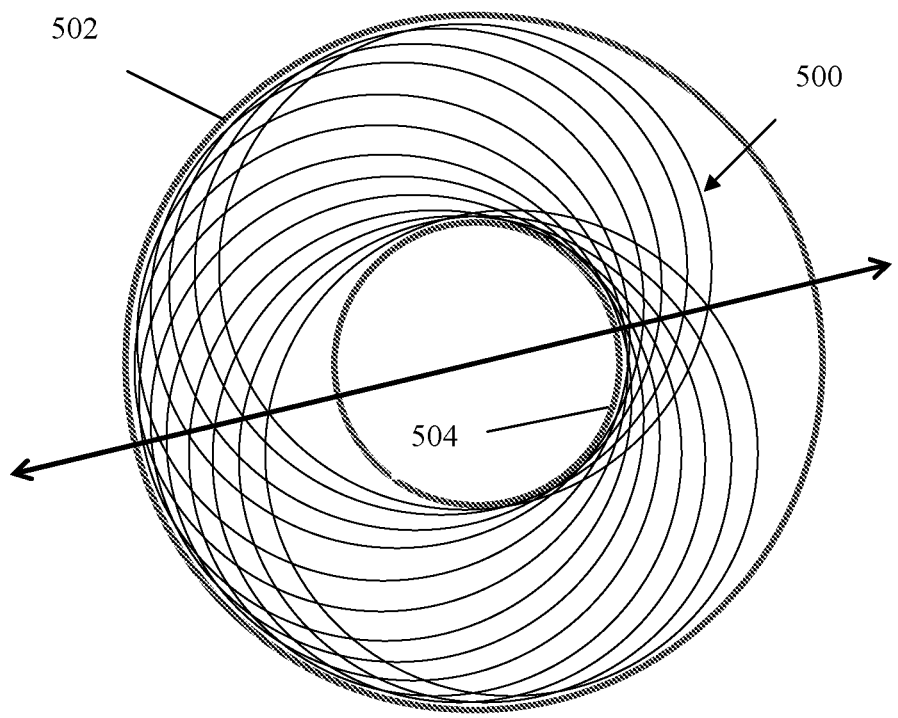
FIG. 5 shows the formation of caustic patterns by "Debye rings" formed at a detection surface of an X-ray scatter gathering apparatus, at a point in a region along a primary axis in which the caustic rims are divergent from a "hotspot" at which the Debye rings overlap with a maximum intensity.

FIG. 5 illustrates this scenario for a transmission mode opening rim 504 where a set of Debye rings 500 have a radius, which is greater than the radius of the primary radiation beam 128. Again this opening rim is within the area bounded by the outer rim 502.

If the two theta x-ray diffraction angles are less than the half opening angle of the primary beam then only opening rims can be produced as the rims that form inside the outer rim both diverge from the specimen and cannot form a hotspot condition. Another special case is when the two theta diffraction angle is equal to the half opening angle of the primary beam. The resultant rim is formed by Debye rays, which are parallel to form a tubular right cylinder. The rim radius is independent nominally of the separation between the detection surface and the specimen.

Figure 6:
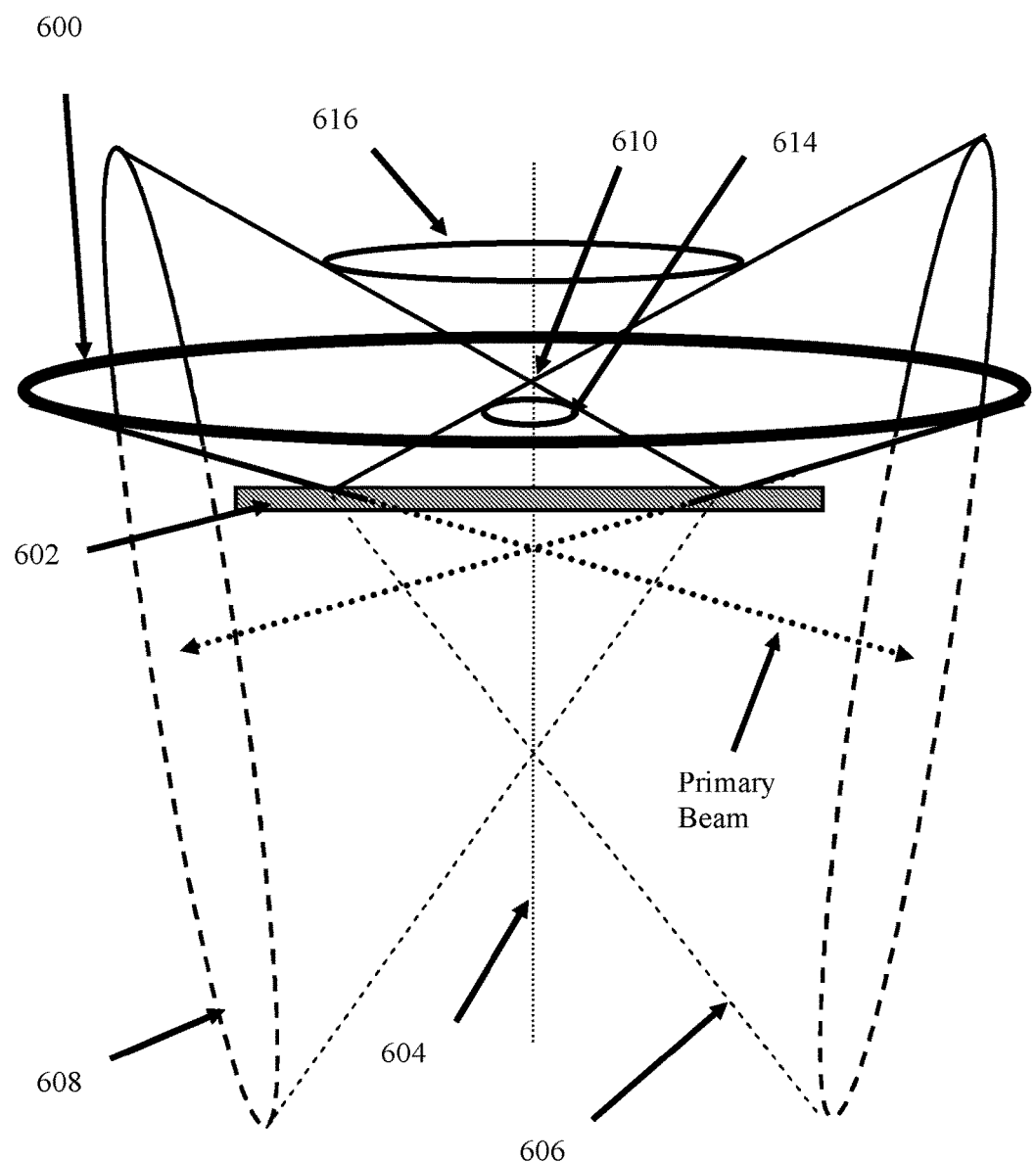
FIG. 6 shows aspects of the formation of caustic rims by a continuum of Debye rings, for an X-ray scatter gathering apparatus comprising a ring X-ray source and operating in an example of a front reflection mode.

Rims may also be produced by employing a ring source of collimated primary X-rays as illustrated in FIG. 6 where the convergent tubular primary beam can be employed in reflection mode. X-ray ring source 600 has a primary axis 604 and directs radiation towards a sample 602, generating Debye rings 606, 608. The dotted section is attenuated and/or not accessible for measurement in reflection mode. Closing rims (example, 614) and opening rims (example, 616) are formed on opposite sides of a hotspot 610.

Figure 7:
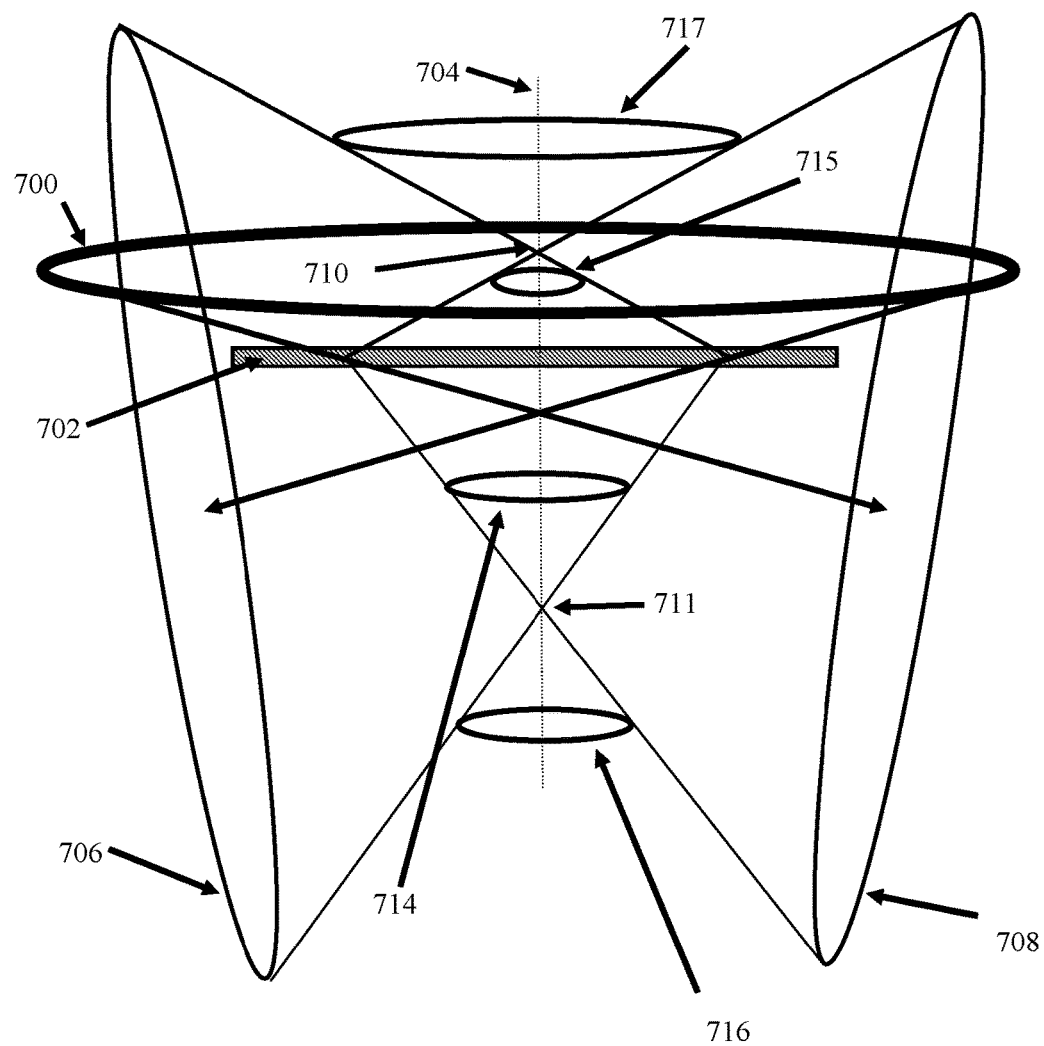
FIG. 7 shows aspects of the formation of caustic rims by a continuum of Debye rings, for an X-ray scatter gathering apparatus comprising a ring X-ray source and operating in a combination of both front reflection and transmission modes.

It is also possible to simultaneously collect transmitted rims, as illustrated in FIG. 7, showing reflection mode combined with transmission mode employing a ring source producing a collimated convergent tubular beam of primary X-rays.

Again, an X ray ring source 700 has a primary axis 704 and directs radiation towards a sample 702, generating Debye rings 706, 708. In this embodiment, because both transmission and reflection mode data are being used, there will be a reflection hotspot 710 and a transmission hotspot 711. There will also be separate sets of closing inner rims (examples: 714, 715) and opening inner rims (examples: 716, 717) for each of the transmitted and reflected parts.

In reflection mode one or more sensors are placed between the source and the sample. In transmission mode one or more sensors are positioned on the opposite side of the sample with respect to the source. In the combined transmission and reflection mode of FIG. 7, two sets of sensors are required, one on each side of the sample.

Reflection may be the only solution for scanning/imaging applications that requires a single sided inspection such as scanning objects, which are too large, immovable, or otherwise inaccessible e.g. a potential bomb threat that cannot be moved away from occluding structures such as walls (or behind/in a wall); or surface materials that require analysing such as a cave painting or forensic scenario. In other words two types of scenario:

one sided inspection of a volume;
or the sample is on the surface of a thicker structure and the thicker or inaccessible structure is of no analytical interest.

In general, rims do not have to be continuous. They may be partially formed or discontinuous dependent upon the shape and relative orientation of the sample with respect to the primary beam and detection surface. This holds for any arrangement and imaging mode.

The figures illustrate only a small selection of Debye rings. It will be appreciated that in reality there is a continuum and the end effect of the different scenarios of closing and opening rims illustrated for example in FIGS. 2 and 5 may appear similar, namely, inner and outer rims at the same radial positions.

Normal radiation absorption imaging, such as X-ray absorption imaging, concentrates on collecting absorption data, which in the example apparatus of FIG. 1 would involve collection and analysis of the main radiation beam 128. WO 2011/158047, which is hereby incorporated by reference, mentions the possibility of detecting scattering (diffraction) data at a "hotspot" in the centre of the circle formed by the main radiation beam 128, where Debye cones overlap. The z-position at which a spike in signal intensity (hotspot) is detected gives information about the scattering angle(s), which is characteristic of the material forming the sample under test.

However, according to the present disclosure, diffraction data is sampled at the inner and outer caustic rims defined by the continuum of Debye cones, which represents a significant departure from known techniques.

An image of the object is formed by combining subsampled raster scanned images from different radial positions. The scanned imagery obtained along one radial direction, at rim intersections, is primarily determined by the incident angle of the generator ray and is independent of the diffraction angle. Successive images obtained around a rim, at incrementally different radial positions, each produce parallax along the direction determined by their generator ray and its projection of the object under inspection. The angular offset between each successive image enables the presentation of 3D/parallax information through the relative rotation of the features in a visual display and/or binocular stereoscopic display and the synthesis of slice imagery. The parallax needs to be taken into account when reconstructing the image.

Therefore, geometrically matched perspective views may be produced from a series of different rims along one radial direction. Each rim represents a specific two theta diffraction angle. A closing inner rim and an outer rim produced by the same Debye ring continuum (and sampled along the same radial direction) will produce geometrically identical scanned imagery, which may be summed to enable a large increase in the signal to noise ratio for a specific two theta angle.

Sampling different rims along one radial direction enables a series of geometrically identical perspective views to be produced as determined by a single generator ray. The number of matched views for one radial direction is determined by the number of different rims sampled along this direction, where views are "matched" if they exhibit nominally identical parallax direction and magnitude. Matched views can be registered with respect to one another to combine and enhance signal deficiencies or reveal complete shape information, enhanced detail or varying material properties that may be present in the individual images.

Figure 8:
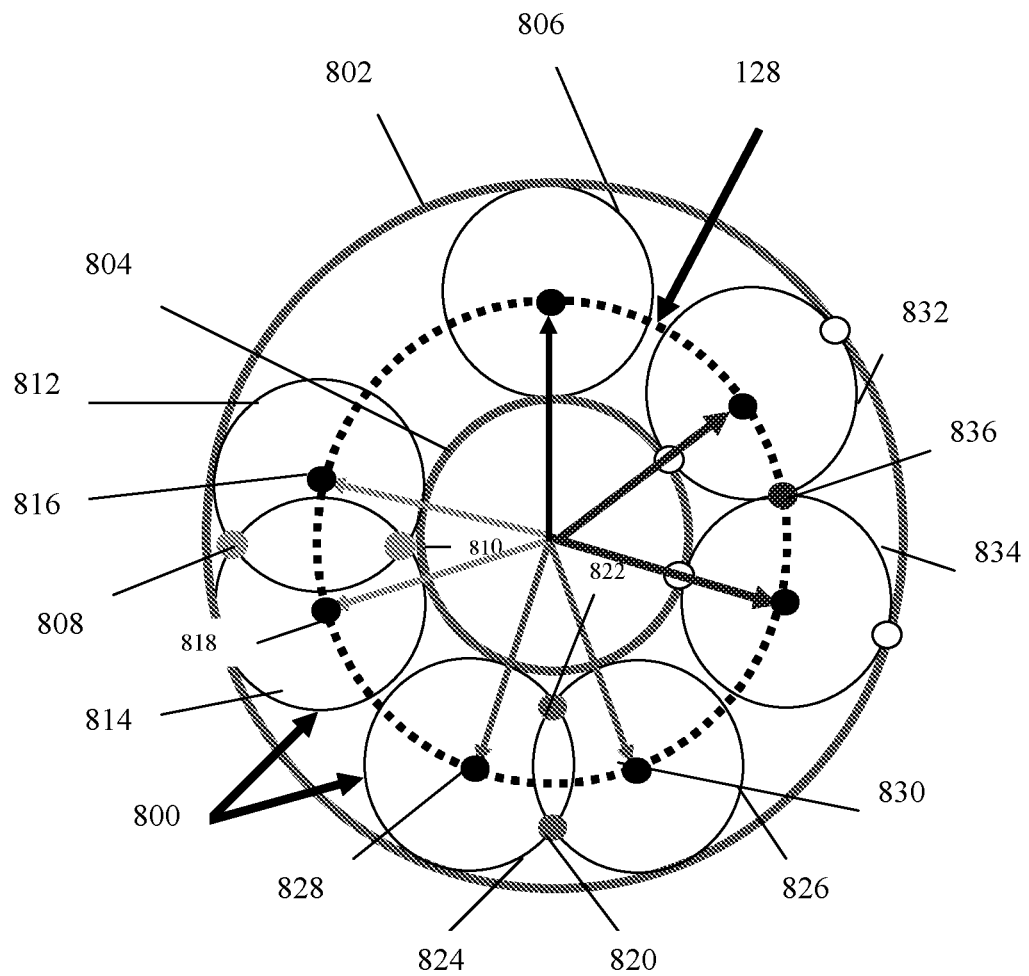
FIGS. 8-12 show further aspects of caustic patterns of Debye rings formed at a detection surface of an X-ray scatter gathering apparatus.

FIG. 8 illustrates a set of Debye rings 800 forming outer and closing rims 802, 804 in similar manner to that already illustrated in FIG. 2. Although there are an infinite number of Debye rings in the continuum of Debye rings formed by an image, it is instructive to consider each Debye ring as an infinitesimally thin ring. In effect, for the case of closing rims the intensity generated at the inner and outer rims will at each angular position be the result of a single Debye ring, illustrated here at 806. Each point in the focal plane between the rims will be generated by only two Debye rings. Further, a pair of Debye rings that just touch without overlapping each other will define a single common intersection point, while any pair of intersecting Debye rings will define (only) two common points of intersection with each other. For example, as shown in FIG. 8, the signal at (the infinitesimal) points 808 and 810 is generated only by Debye rings 812, 814 which correspond to the Debye rings at angular positions 816, 818 of the primary radiation beam 128. Similarly, the signal at (the infinitesimal) points 820, 822 is generated by Debye rings 824, 826 at angular positions 828, 830. Meanwhile, the diffraction signal intensity generated at the position of the primary radiation beam 128, represented at 836, is the result of only two Debye rings 832, 834 which just touch at their respective edges.

Figure 9:
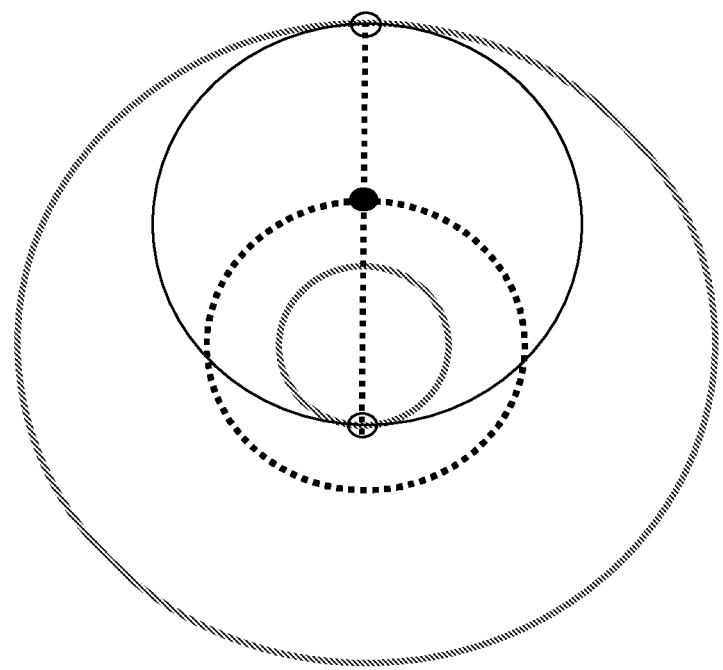

A similar situation exits for an opening rim as illustrated in FIG. 9 except here the outer rim and inner rim matched pair (along one radial direction that in this instance extends across the centre point due to the opening rim) are in different relative locations in comparison to the closing rim condition in FIG. 8. The opening rim condition means that matched perspectives can occur on a radial line extended "beyond its centre point". This scenario also means that an opening rim along one radial direction will belong to the diagonally opposite generator ray. This condition is resolved by using tomosynthesis as the resultant imagery has to be focussed along the reverse radial direction.

Figure 10:
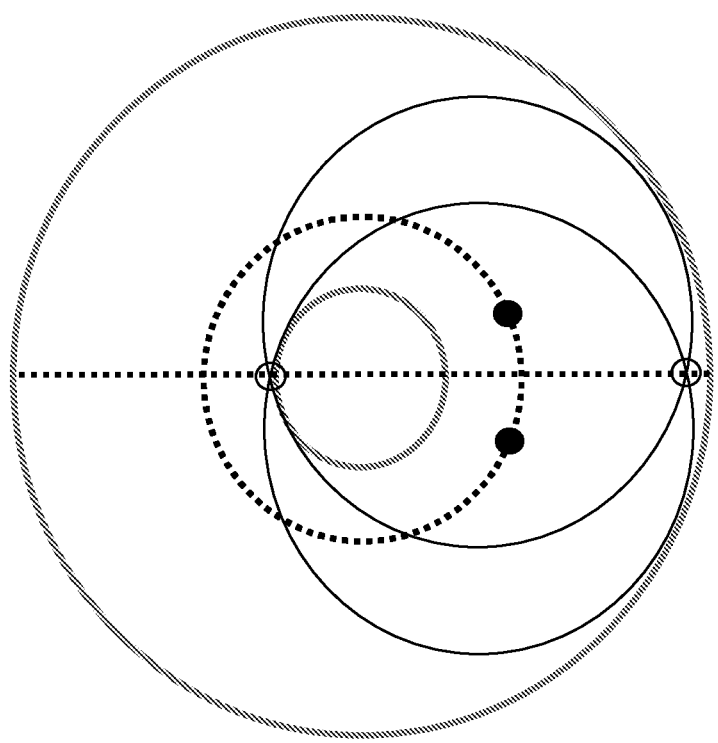
Figure 11:
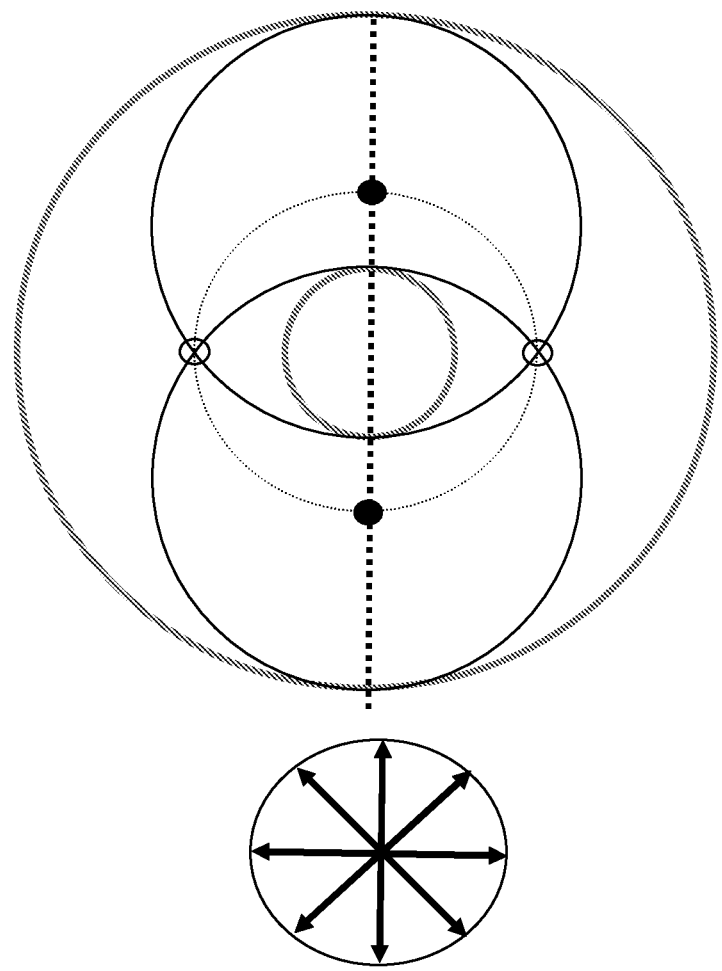

Near rim sampling for inter rim sampling is illustrated in FIG. 10 where the angular separation of the two generator rays is indicated. The maximum angular separation between the two generator rays for opening rims, which equals the diameter of the tubular primary beam at the specimen, is illustrated in FIG. 11.

Effectively, for each Debye ring pair spacing two different generator rays contribute to the parallax in each scanned image. The greater the angular separation between the two generators the more disparate the two signal contributions become. The convolution of the inspection space with the two generator ray apertures (each recording parallax along different directions) is equivalent to scanning the inspection volume with each aperture in isolation then summing the two perspective images at the correct relative registration and intensity weightings in x-axis and the y-axis.

Therefore, a single image produced by raster scanning at a sampling location between inner and outer rims, along one radial direction, is equivalent to convolving the space under inspection with the two generator ray apertures. The direction and size of the separation between the two apertures is a function of the two theta diffraction angle (the half opening angle of the Debye cones), tubular primary beam topology and the Z height of the sample or in the case of an aggregate of samples/objects the relative location (x,y,z) and orientation of each sample/object within the inspection volume.

Effectively, for each Debye ring pair spacing, there is a separation between the two generator rays, which varies from a minimum that tends to zero, at a rim, up to a maximum equal to the tubular beam diameter. In practice, this situation will require the finite area of the sample i.e. the size of a photosite on a spatially sampling sensor, to be taken into consideration.

Figure 12:
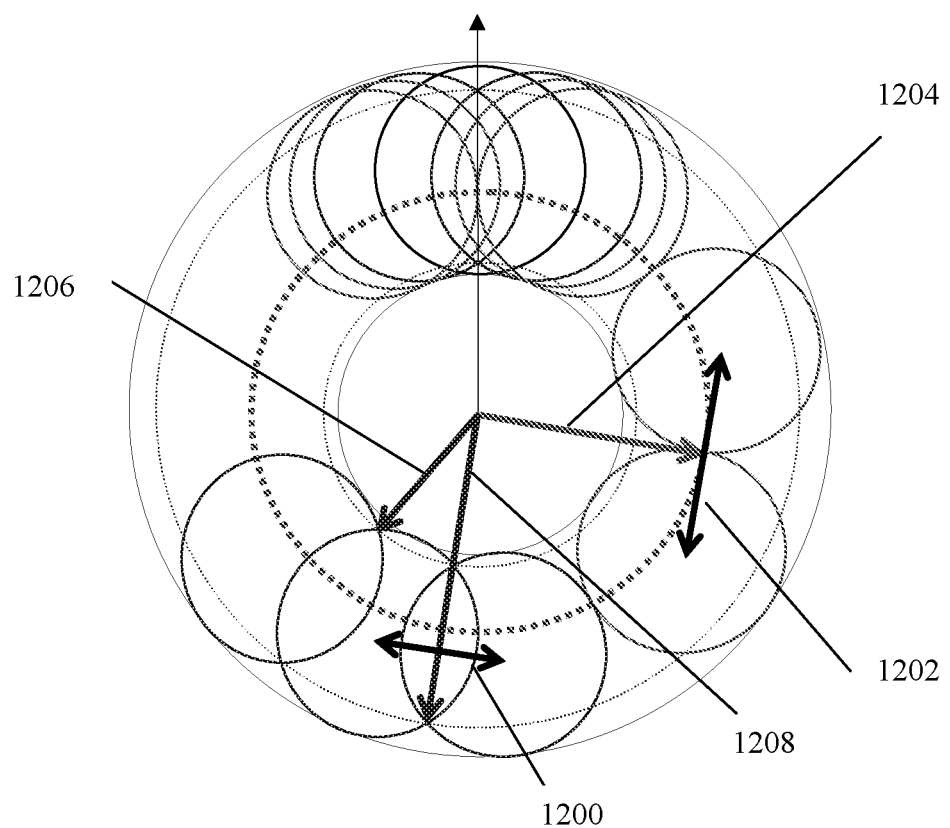

Effectively, for each Debye ring pair spacing, there is an effective annular aperture. The minimum annular width of the aperture tends to zero at a rim. FIG. 12 illustrates two examples of this, showing separation between generator rays as a function of the inter rim sampling position.

The tangential arrows 1200, 1202 indicate the separation between the generator rays. The radial arrows 1204, 1206, 1208 indicate the sampling positions. When the generator rays are separated then each resultant image view is a double perspective view. The separation between these double (but different) views is due to the different contributions (i.e. parallax) provided by each generator ray.

In practice, the finite sampling area will capture contributions from more than two generator rays especially near the inner rim (and to a lesser extent the outer rim) where the 'crossover' pattern between different rims is dense (as in FIG. 2).

Therefore, more than two perspective views may be present in each image (appearing as discrete perspectives of the object under inspection at different translated locations around a circular path). Furthermore, these multiple perspective views may be well separated.

Therefore, a single sampling element can provide a single image but also contain different perspective views of the object under inspection. These views may be non overlapping and once separated from each other be treated as per-rim sampled images (although reduced in the total number of different perspective views).

Figure 13:
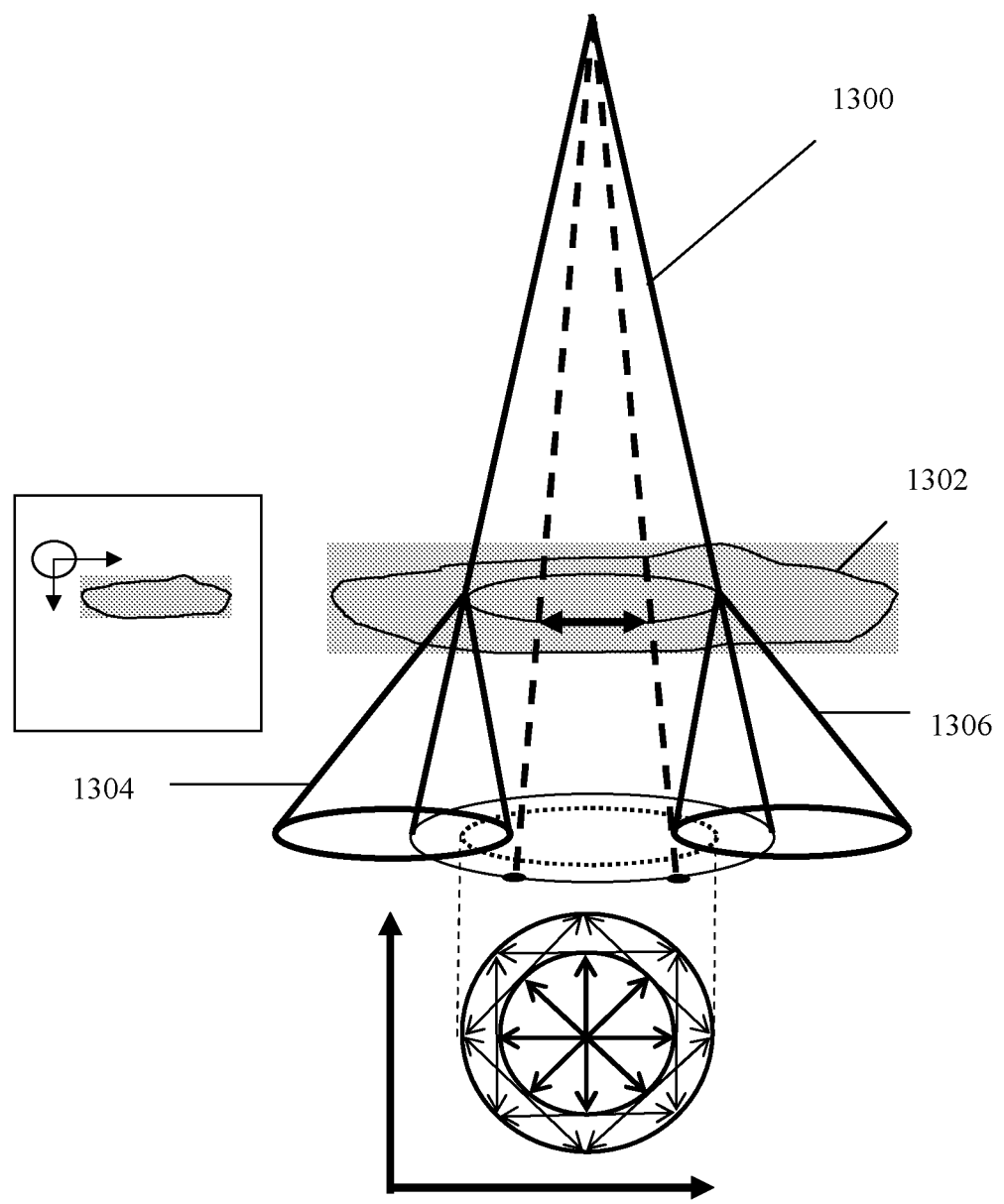
FIG. 13 shows an X-ray scatter gathering apparatus in which a focal plane image is convolved with an apparent annular aperture.

Effectively therefore, a composite image can be formed by tomosynthesis employing a full set of rim-derived X and Y raster scanned perspective images which produce a focal plane image convolved with an apparent annular aperture, which has a zero effective aperture at a rim. An example of the annular aperture is illustrated in FIG. 13, which shows a tubular beam 1300 interrogating an object 1302 producing Debye cones 1304, 1306. The tomosynthesis provides the z height information for the focal plane image to enable the two theta diffraction angles to be calculated automatically. Therefore, the spatial origin of one or more diffraction peaks, corresponding to focal plane features can be used to identify material properties.

The term "tomosynthesis" as used herein refers generally to the production of a composite image by processing multiple electromagnetic rays at different relative registrations to provide one or more focal plane images.

The rays may be collected in transmission mode, reflection mode, or a combination of the two, and the composite image that is produced may be two or three dimensional.

FIG. 13 shows further aspects of the disclosure in which the combined effect of the inter-rim sampling is illustrated. Each individual image is the result of a convolution involving a double aperture. The effect of this at the focal plane is equivalent to a convolution of the focal plane image with an annular aperture whose diameter is determined by the separation of the convolving apertures. A deconvolution of the inter-rim focal plane imagery will enable useful signal to be recovered from this 'blurred' region.

Figure 14:
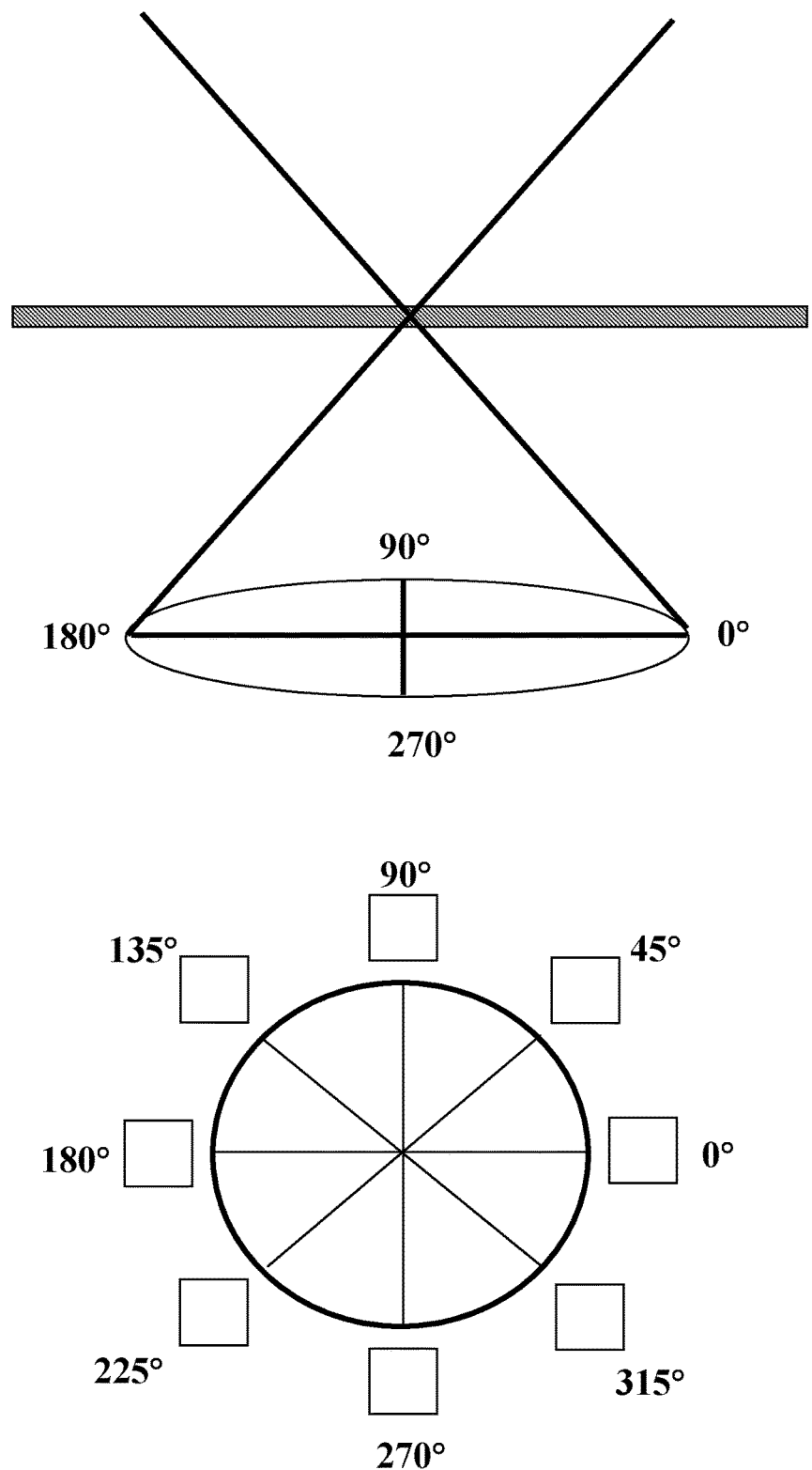
FIG. 14 shows aspects of an object visualisation technique.

FIG. 14 shows how voxels in a sample are interrogated around a circular path (corresponding to different radial directions) to reveal material properties e.g. preferred orientation, grain size, density. These properties may be mapped by scanning a planar sample or for samples with extended shapes (or an aggregate of such samples).

This spatial information may be established using different methods. These include movie sequences showing image features being translated around a circular path as a function of their relative position with respect to a convergence or datum plane. Alternatively, the rotation of the object(s) under inspection can be arranged to conserve the direction of parallax along one axis. This latter technique can be used to display a binocular stereoscopic image sequence by maintaining the direction of parallax in the visual display along the horizontal display axes but in opposite directions for the left and right perspective view sequences. Also, a sequence or stack of focal plane images, produced by tomosynthesis, can be displayed as a 'stepwise' movie along the z-axis. These visualisation methods may be combined in different ways to enhance the interpretation of the two dimensional or three dimensional shape, orientation and/or material properties of an object or process under inspection.

Three examples of visualisation techniques will now be described:

Circular Translation According to Depth Dependent Radii:

Replay perspective images (or frames) according to angular progression. In this type of display features appear to be translated around a circular path as a function of their relative separation in the Z axis, in the plane of the visual display i.e. parallel to the plane of the sensor surface. All points or features that occur at the convergence plane will appear stationary while other points/features undergo a circular translation determined by their perpendicular distance from the convergence plane. This plane is analogous to a focal plane, produced by tomosynthesis, and is a plane of depth that subtends the object in the display and exhibits zero motion (or parallax). This plane can be moved to any point within the inspection volume by effecting a change in the relative radial convergence (along the radial image collection angle) of the perspective views. Thus, the convergence plane can be moved, automatically or interactively, through the object under inspection to reveal structures or features or material properties relative to the object features above and below the convergence plane. In addition, relative depth information may be revealed through motion effects to gain an enhanced spatial understanding of the true nature of the object(s) under inspection.

Figure 15:
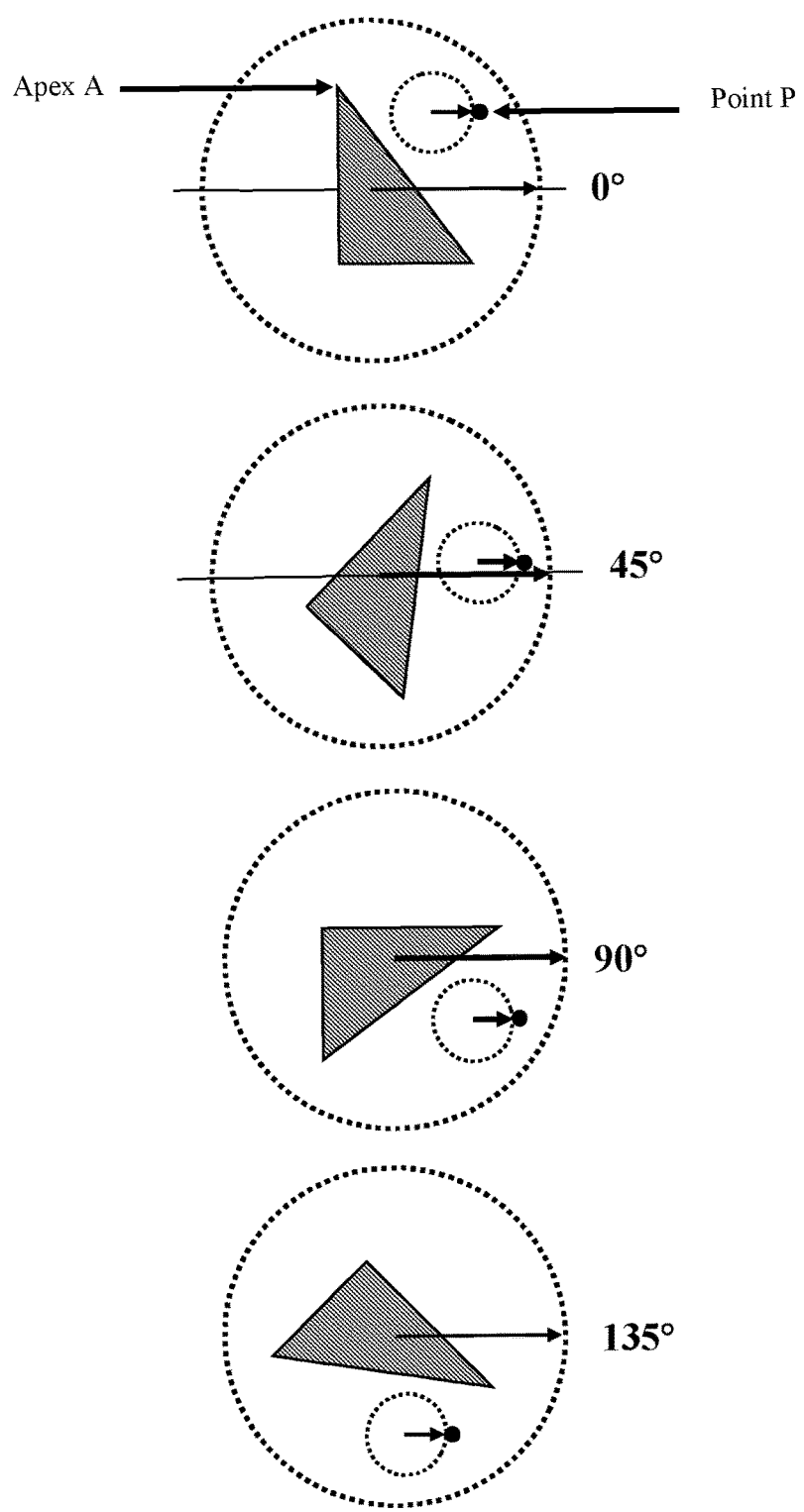
FIG. 15 shows an object visualisation technique, comprised of circular motion in which a direction of parallax is constrained to one direction.

Circular Motion in which the Direction of Parallax is Constrained to One Direction as Illustrated in FIG. 15.

To accommodate this constraint the objects themselves rotate about a central axis. The relative motion between object features remains as before. This alternative visual display requires first rotating each frame about its centre point before displaying the resultant movie (as before). The angle of each rotation is determined by the radial image collection angle; for example 0°, 45°, 90°, 135° as per FIG. 15. A datum angle is chosen, which in this example is 0°. Therefore, the image obtained at 90° is rotated about its centre point by that angle and so forth. The final sequence of frames can now be displayed to reveal a 360° rotation of the object under inspection. The resultant ray geometry is equivalent to rotating the object about its central axis in an inclined parallel beam of radiation (i.e. synchrotron beam) incident upon a planar 'snapshot' sensing surface. The rotation axis is normal to the sensor surface. In this type of image sequence the parallax direction is fixed through the choice of the datum angle. The relative path of point P with respect to a converged object point A (i.e. one that exhibits nominally zero parallax) remains unchanged in comparison with the first type of rotation. However, all objects rotate through 360 degrees. The resultant rotational motion is created in a visual display by manipulation of a perspective views obtained by a linear (x,y) scanning of the object under inspection by a tubular primary beam. This motion can be stopped and started interactively to inspect and look around spatially complex structures e.g. a suitcase or cargo in aviation security screening, to reveal the true nature of the objects shape and their relative positions within an inspection volume.

Figure 16:
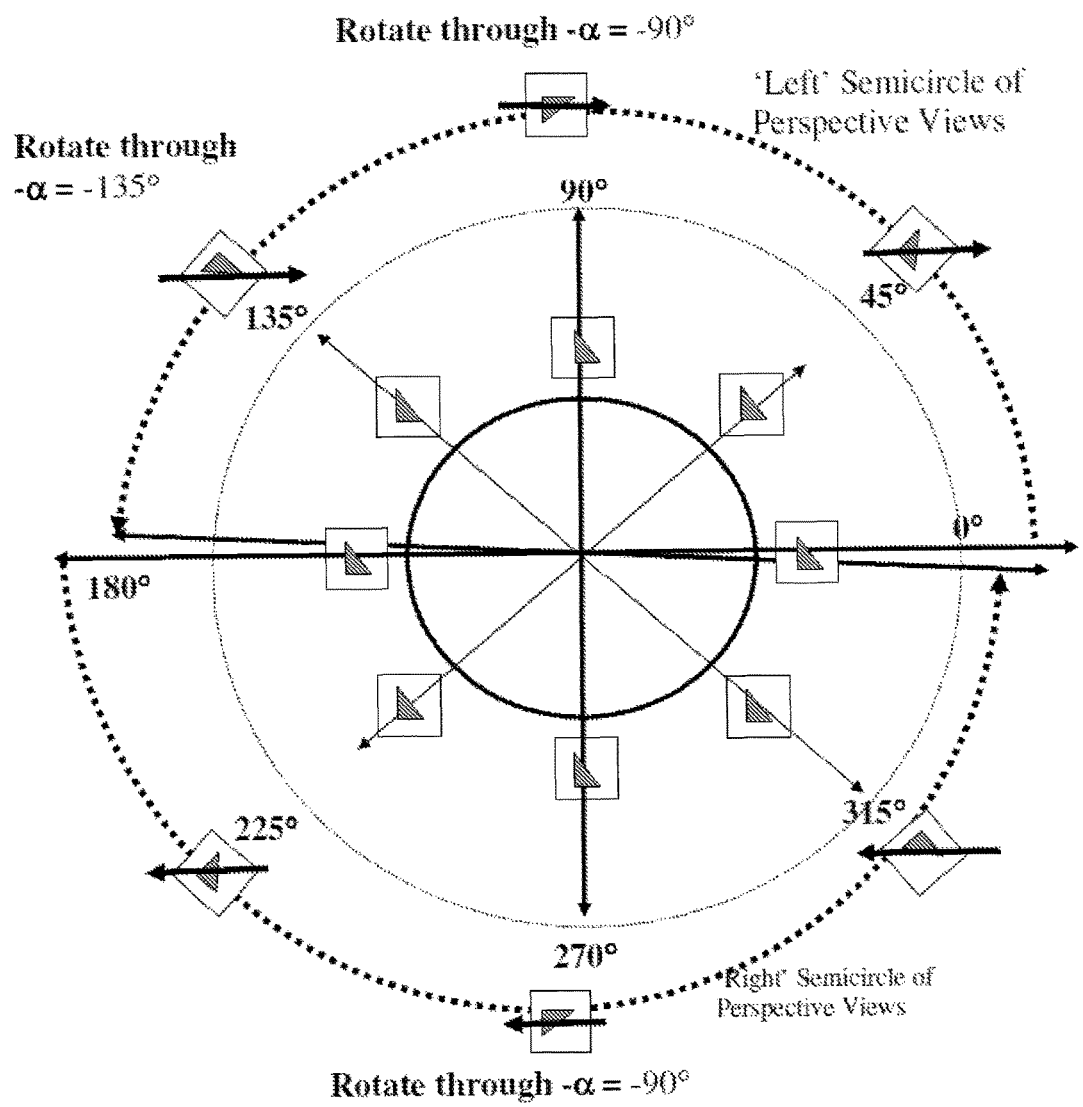
FIG. 16 shows a visualisation technique, where perspective views may be considered as a sequence of stereoscopic pair images.

Stereoscopic Imaging as Illustrated in FIG. 16.

Here the perspective views may be considered as a sequence of stereoscopic pair images. The incremental angular progression of image pairs will exhibit parallax comprised of a horizontal and a vertical component. The epipolar line (or linear search space direction for corresponding features) will be determined by the generator ray (as it determines the direction of parallax along one radial direction). The length of the search space will be determined by the angular separation of the generator rays. The automatic or manual identification of corresponding features can be employed to calculate coordinate measurement information to enable the x,y,z coordinate positions to be identified.

Diagonally opposite stereoscopic image pairs i.e. 0° and 180° shown in FIG. 16 produce maximum depth sensitivity or minimum detectable depth increment as their generator rays are at a maximum angular separation i.e. they exhibit the maximum rate of change of parallax with respect the z-axis.

Each diagonally opposite image pair may be viewed as a binocular stereoscopic image by arranging for the direction of the parallax (parallel to the radial direction of the generator ray) to be along the horizontal direction in a binocular stereoscopic display. However, the parallax directions for the left perspective and the right perspective are opposite along this horizontal display axis as illustrated in FIG. 16. These horizontal directions are conserved by rotating each individual image around its centre point to align their radial image capture direction along the horizontal display axis. Thus, for a 360 view system (i.e. 360 different radial directions or image capture/scanning elements) a sequence of left perspectives, at 1° angular increments, will produce 180 different left perspective views (0° through to 179°) and also 180 different right perspective views (180° through to 359°) to produce 180 different binocular stereoscopic images. The resultant binocular stereoscopic image pairs may be viewed as a static pair or as a movie/dynamic sequence in which the objects under inspection will appear to rotate around 180°. The notion of left and right perspectives is arbitrary due to the rotational symmetry of the primary tubular beam producing parallax along different radial directions over 360°. Also, because an individual image produced with transmitted radiation does not contain any cues to depth then transposing 'left' and 'right' views in a binocular stereoscopic display will reverse the parallax and the resultant fused image will appear reversed in depth i.e. features that were in the foreground will now appear in the background and so forth, and the depth axis will have flipped through 180° about the convergence or zero parallax plane. The control of the 'reverse depth effect' can be usefully incorporated into an operator's visual display to facilitate the best view of an object under inspection. Also, a control of the relative position of the convergence plane within the inspection volume can be used to control the apportionment of positive and negative parallax in the display and therefore, the relative position along the normal to the display axis of the binocular stereoscopic image. The sum of the absolute magnitude of the positive parallax and negative parallax is a constant once the imagery has been captured. All these interactive visual control features are made possible by the parallax generated along the different radial directions and can greatly enhance a human operator's search for anomalous, threat or contraband objects/materials in e.g. security scans of luggage or defective items in industrial inspection applications.

The display requires an appropriate stereo viewing mechanism e.g. synchronised shuttering (polarised) spectacles or an auto stereoscopic display. A sequence of diagonally opposite images may be arranged to produce a binocular stereoscopic sequence in which the object under inspection would appear to rotate, about an axis normal to the display screen, whilst being viewed in binocular stereo by an observer. Different material properties could be displayed simultaneously or separately to provide a dynamic visual interpretation of the relative three dimensional location of these properties.

The inventors have realised that sampling of the high intensity diffraction rims along a radial direction during an X and Y scan of an object under inspection will produce nominally identical spatial information in the resulting perspective images. independent of the two-theta scattering angle. Inter-rim sampling produces perspective views, which exhibit parallax in more than one direction, where each different directional component is independent of the two-theta scattering angle.

Now, a particular crystal structure of a sample under test will yield a unique pattern of angular distribution of scattered intensity for a specific Debye ring. This means that the continuum of Debye cone elements form substance dependent caustics which can be sampled and quantised by a sensor.

Depth information is identified along radial paths that are independent of the scattering angle. This property enables, with appropriate synthesis, direct tomography or laminography.

Therefore, images of extended objects directly attributable to individual diffraction lines may be produced and combined with other diffraction line views to provide material identification and characterisation.

The amount of parallax depends upon the opening angle of the interrogating tubular beams and the z-axis component subtended by the object under inspection. In the special case of the interrogating tubular beams having a relatively small opening angle, then the information provided by parallax effects will be minimal, or zero in the case of an interrogating tubular cylinder (which would require a circular source). In this case the resulting image is a bright 2D image for which the focal plane subtends a relatively large orthogonal component and will tend towards the geometry of a single planar image. This "zero depth" image could help to mitigate any deleterious effects associated with grain size and/or preferred orientation especially when using a point source. Images are still summed from different locations about the axis of symmetry but this time the tomosynthesis has no depth sensitivity and produces a single thick slice image.

This concept may also help avoid problems associated with relatively intense "point" sources, which tend to expand with increasing energy densities. Practical high power point sources could be collimated in such a way to avoid the blurring produced by the "unavoidable" fat cross section of a pencil beam by employing a tubular pencil beam.

The disclosure enables chemical signature and three-dimensional information to be captured simultaneously using coherently scattered signals alone. This is due to the tubular coupling of the primary and diffracted beam topologies to produce stable radiation diffraction caustics incident upon a sensor as described above. This overcomes the fundamental problem of low intensity signals originating from unknown locations in an inspection volume, which has been a major barrier to the development of real-time diffraction imaging applications. The intensity of coherent scattering of diffraction phenomena is orders of magnitudes smaller than the intensity of the interrogating radiation beam.

Using the concepts of the disclosure, unique diffraction signatures may be possible for many different crystalline materials including for example manufactured materials such as metals, alloys, ceramics or cements; minerals such as rocks, salts and soils; organic materials such as drugs, chemicals, sugars proteins and so on. The disclosure has applications in many different areas including for example and without limitation, security imaging, forensics (for example drug detection), non-destructive testing and evaluation, quality assurance and process control in production or manufacture of physical goods, instrumentation and medical diagnostics.

A common problem encountered in the field of X-ray diffraction imaging is that of the preferred orientation of crystalline materials. In an ideal case, a sample would comprise particles oriented at random and the diffraction spectrum would be the same for any sample orientation. However in real samples there will be a preferred orientation, which is derived from the crystalline lattice structure of the sample. This means that the diffraction peaks change depending on the orientation of the sample, meaning that materials can be incorrectly identified or not seen at all (especially in a scanning system). Traditionally, to account for this type of variation it is important to prepare a sample very carefully and potentially systematically change the relative incident angle of the integrating beam to obtained signals from preferred regions of the structure under inspection. However, this is not possible in a "real world" context such as screening baggage at an airport, where the sample is not prepared under laboratory conditions.

Figure 17:
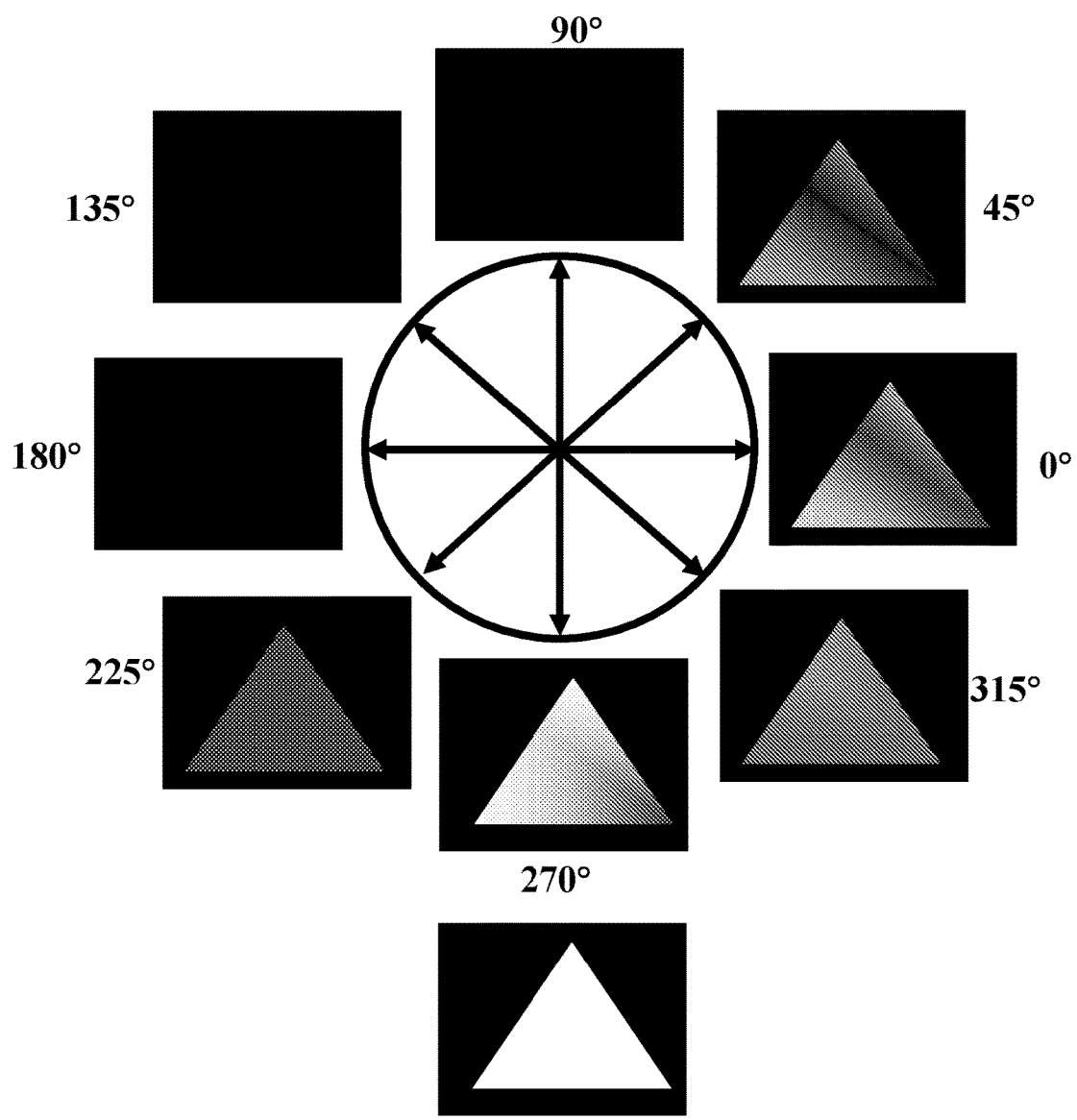
FIG. 17 shows a visualisation technique in which different perspective views highlight a preferred orientation of crystallites along a specific radial direction.

The present disclosure significantly ameliorates the problem of preferred orientation, because a series of perspective views are used in building up the image. A sequence of images attributed to different radial directions is illustrated in FIG. 17. The focal plane image is the sum of the views along each different radial direction and may be produced by one or more different diffraction angles. This approach enables the detection of and identification of objects, features or shapes, which may not be present at all or only partially in individual perspective views and also facilitates the analysis of preferred orientation.

Visual Display and Software Analysis

Analytical visual display and software analysis: The in focus portion of each frame may be displayed in sequence (i.e. incremental change in angular separation) to produce a movie depicting the changes in preferred orientation over the angular range of the primary beam at the locality of the focal plane.

Another type of movie could employ the raw frames to combine the preferred orientation effects with motion (due to parallax changes) to produce 3D information in a visual display.

Software techniques can be applied to automatically store and extract the information for further analysis e.g.

volume elements (x,y,z) could be identified and attributed with material properties.

Another common problem encountered in the field of X-ray diffraction imaging is that of the differing grain size of crystalline materials. Even materials of the same type can have a variety of grain sizes, the variation of which has an effect on the diffraction peak intensities that are generated and means that materials can be incorrectly identified or not seen at all.

Figure 18:
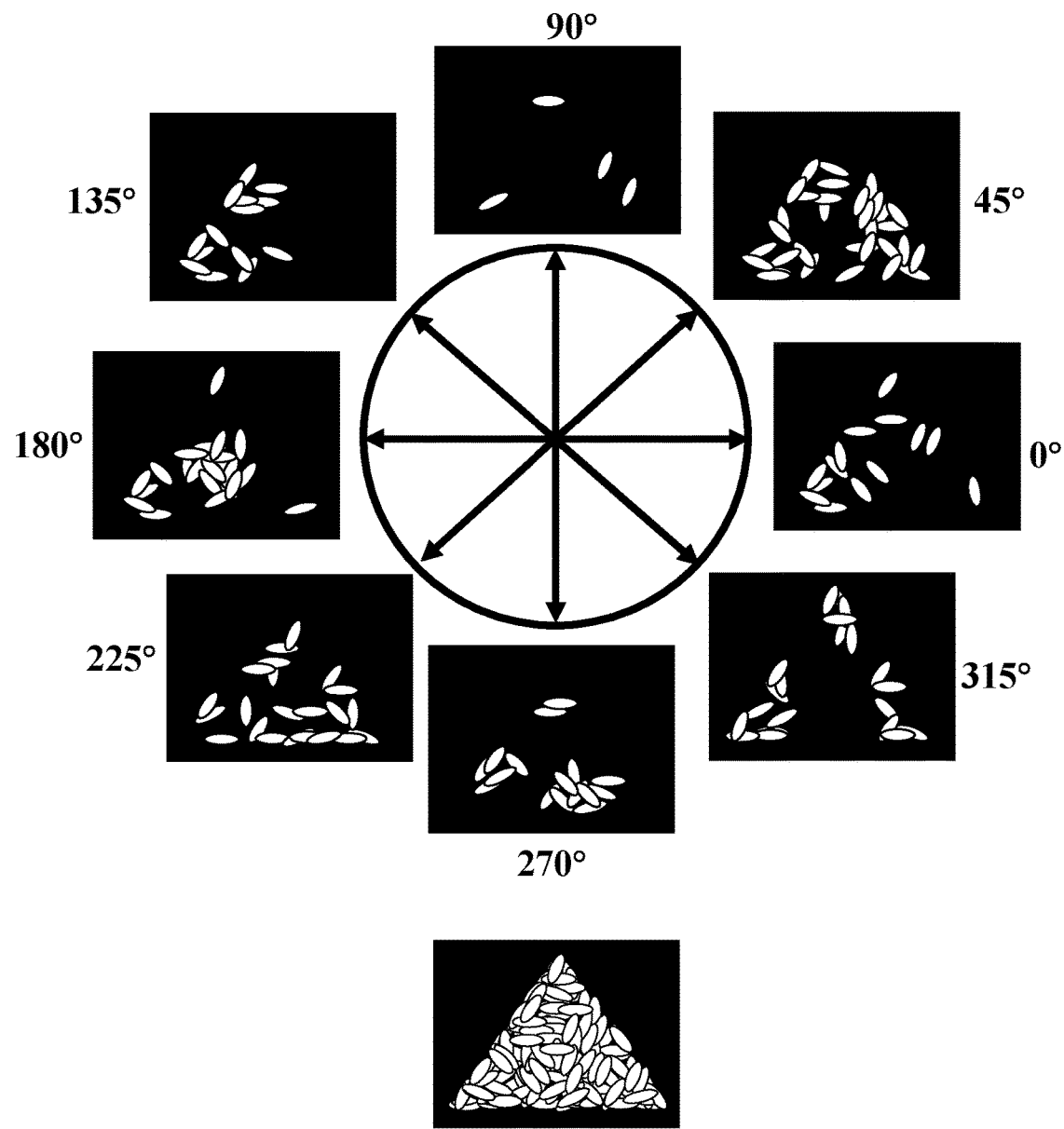
FIG. 18 shows a visualisation technique in which different perspective views comprises grains diffracting along a specific radial direction.

The present disclosure significantly ameliorates the problem of variable grain size, because a series of perspective views are used in building up the image. This means that the effects of variable grain size may be integrated across many perspective views to produce enhanced imagery that has richer spatial detail and shape information as well as more robust materials identification. One effect of grain size is shown in FIG. 18. The focal plane image is the sum of the views along each different radial direction and may be formed using one or more different diffraction angles. This approach enables the detection of and identification of objects, features or shapes, which may not be present at all or only partially in individual perspective views. This approach also facilitates analysis of grain structure and orientation.

Visual Display and Software Analysis

The in focus portion of each frame may be displayed in sequence to produce a movie depicting the changes in grain orientation and structure over the angular range of the primary beam at the locality of the focal plane.

Another type of movie could employ the raw frames to combine the grain information with motion due to parallax changes to produce 3D information in a visual display.

Software techniques can be applied to automatically extract this information for further analysis e.g. volume elements (x,y,z) could be identified and attributed with material properties.

The perspective images that are captured according to the disclosure may be relayed in a special spatial structure from visual motion mode. A movie sequence of perspective images, which exhibit rotating features, in planes parallel to sensor surface, as a function of their relative depth (Z axis) in a visual display.

The perspective images may be sequenced to produce a movie of static features/samples or objects in, which the effects of preferred orientation and or grain size can be, viewed as the incident angle of the generator ray changes and or the diffraction scattering angle changes. The movie frames may combine imagery produced at different scattering angles to enable enhanced materials identification and analysis. Perspective images produced at different scattering angles may be mapped together to provide colour encoding via a corresponding pixel positions input to a lookup table to highlight threat or contraband materials in security scanning or highlight faulty material composition, foreign bodies or contaminates in process control or manufacturing processes. These enhancements and viewing methods may be combined with the spatial structure from motion mode to provide 3D dimensional visual information.

The accompanying figures show operation of the disclosure in various embodiments using transmission imaging. However, it will be appreciated that the disclosure may be equally applied in backscatter mode.

It is also to be appreciated that the concept of the disclosure is inherently scalable.

As mentioned above, the principles of the disclosure can be applied for either transmission mode or reflection mode, meaning that it may be applied for Debye cones or parts thereof that are either reflected from the sample or transmitted through it. It is to be appreciated that there does not have to be a one-to-one correspondence between transmitted Debye cones and "forward" Debye cones (those which propagate in a direction with a positive component in the direction of the primary radiation after interaction with a sample), or between reflected Debye cones and "back" Debye cones (those which propagate in a direction with a negative component in the direction of the primary radiation after interaction with a sample).

Figure 19:
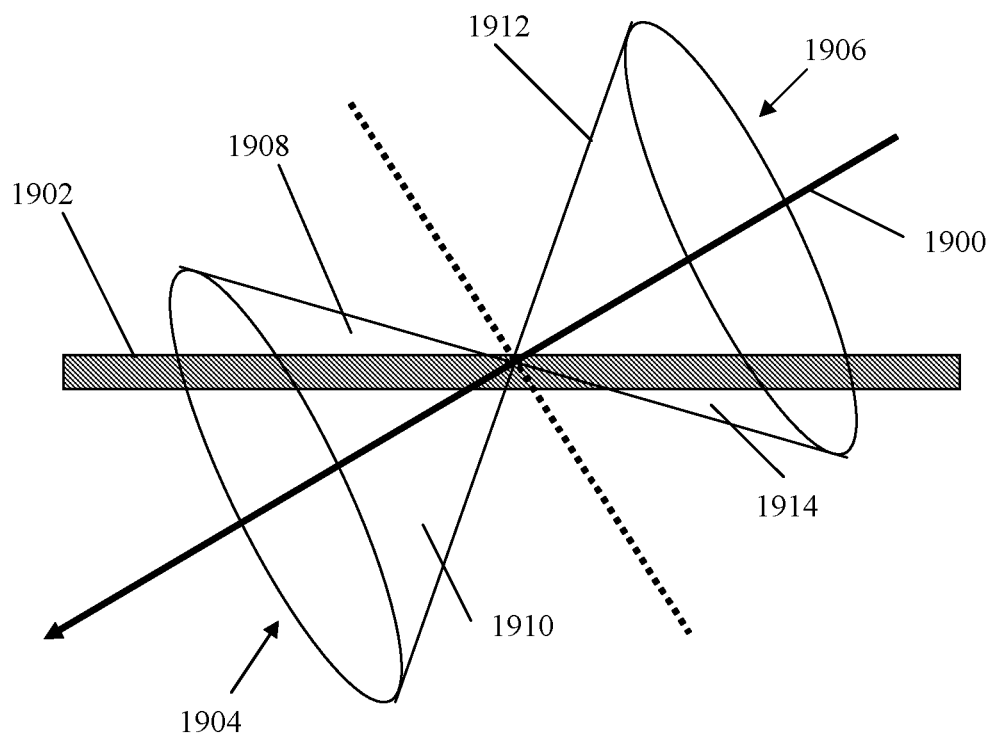
FIG. 19 shows how transmission and reflection mode Debye cones are defined.

This difference is illustrated in FIG. 19. A primary beam 1900 incident upon a sample 1902 produces front and back Debye cones 1904, 1906. The front Debye cone 1904 comprises a front reflected portion 1908 and a front transmitted portion 1910, while the back Debye cone 1906 comprises a back reflected portion 1912 and a back transmitted portion 1914.

In the above discussions we have ignored Compton scatter effects (incoherent, inelastic scatter) which are also present in forward and backwards directions. These effects do not produce distinct rings or rim structures. The background signal thus formed can be incorporated into the image and/or material analysis or subtracted out from the perspective views to better detect coherent scatter.

There are various types of sensor (or "detector") that can be used as part of the present disclosure. The sensors may be point (or zero dimensional), line (one dimensional) or area array (or two dimensional). The dimensionality of the detector is dependent upon the application in terms of quantum efficiency, linearity, count rate and energy window, as well as speed and cost.

For example, a scanning application requiring the real time monitoring of the presence and intensity of a specific two theta peak can be implemented using a point detector by sampling a rim for a known sample position in (x,y,z).

Examples of applicable point detector technologies include;

Gaseous proportional counters that exploit multiple ionisations to create detectable pulses for each incident x-ray photon providing proportionality between photon energy and the pulse intensity to enable a degree of energy resolution but not enough for energy dispersive diffraction. Detective quantum efficiency (DQE) is around 50% over the range from 5 keV to 12 keV. The energy resolution is $\Delta E/E$ is around 10%, where E is the energy of a monochromatic beam and, $\Delta E$ is the energy window at full half width maximum of the detector efficiency curve.

Scintillation counters that consists of a sheet of phosphor materials: inorganic e.g. sodium iodide or organic e.g. plastic such as polystyrene, to covert the incident diffracted X-rays into fluorescence coupled to a photomultiplier to convert the visible light flashes into voltage pulses. These have good temporal resolution and high DQE approaching 100% but typically around 80% over the range from 5 keV to 30 keV. In comparison to proportional counters their energy resolution is relatively poor. The energy resolution is $\Delta E/E$ is around 40%, where E is the energy of a monochromatic beam and, $\Delta E$ is the energy window at full half width maximum of the detector efficiency curve.

Solid-state detectors employ the direct detection of X-rays in e.g. lithium doped silicon Si(Li) or lithium doped germanium Ge(Li). The energy window of Si(Li) can be <200 eV to enable angular dispersive diffraction without a monochromator when using white radiation.

One disadvantage is the requirement for low operating temperatures e.g. 77° K requiring liquid nitrogen or Peltier thermoelectric cooling. A Si(Li) detector can have a DQE around 80% from 6 keV to 12 keV. The energy resolution for Si(Li) is ΔE/E is around 2% or 3%, where E is the energy of a monochromatic beam and, ΔE is the energy window at full half width maximum of the detector efficiency curve.

Recent advances in this area include spatially sampling detectors made from high Z materials (around 50) such as cadmium telluride and cadmium zinc telluride (CdZnTe or CZT) and mercuric iodide, which can all work at room temperature.

The above detectors; proportional, scintillation and solid state are known as photon counting detectors as each incident X-ray photon is converted into a counted pulse. Other detectors are integrating detectors in which the X-ray signal produces an analogue electronic signal which represents the X-ray intensity.

Examples of applicable linear detector technologies include;
  Linear or line detectors may straight or curved and comprise an array of nominally identical detection elements or photosites.
  Linear position sensitive proportional chamber employs a long anode wire in a detector chamber full of gas. The difference in readout between each ends of the anode wire enables the readout electronics to determine the X-ray photon counts and their location.
  Line detectors can be configured to cut across rims to provide a relatively fast response in comparison to scanning a point detector over the same two theta angle.

Examples of applicable area detector technologies include;
  Area detectors are used routinely in two dimensional X-ray diffraction systems. They comprise a two dimensional array of sensor elements.
  Charge couple device CCD detector is fabricated from a large semiconductor wafer. These detectors may be may be placed side by side to form a larger mosaic detector.
  Area detectors may be classified as photon counting or integrating detectors as per linear and point detectors.
  Some examples are:
  Multiwire proportional counter
  Image plate (film replacement technology)
  CCD Detector (direct or indirect). Indirect e.g. terbium-doped gadolinium oxysulfide (Gd2O2S:Tb or GADOX or P43)
  Energy resolving discrete or pixelated detector arrays; cadmium zinc telluride (CdZnTe or CZT); germanium and, silicon
  Flat panel CMOS X-ray detectors may be constructed in a modular format to provide different sizes from around; 80 cm² through to 700 cm². These detectors are capable of multi-resolution readout and pixel binning to provide frame rates from 30 Hz at high resolution around 100 Hz over the full detection surface. The detector resolution and gain can be changed dynamically during image acquisition.
  Microgap Detector
  Area detectors can capture multiple rims and interrogate a far greater portion of reciprocal space in comparison to point or line detectors.

In further embodiments of the disclosure, an energy resolving detector may be coupled with a broadband or white spectrum electromagnetic source of primary beams (for example an X-ray source) to enable a hybrid angular dispersive and energy dispersive technique. The energy dispersive detector enables superimposed rim and inter-rim patterns to be separated and detected, identified and extracted for synthesis, image reconstruction and analysis and visualisation. The tomosynthesis would provide the relative location of the diffracting material/object to enable the two theta angles to be calculated. This process could be applied across one or more diffraction scattering angles and detector energy windows to provide materials discrimination and identification information which would be especially useful in highly cluttered scenes such as routinely encountered in security screening.

Also, an energy resolving detector may be employed to preferentially detect, identify, extract and analyse caustic features using a detector with appropriate energy resolution matched to spectral content such as characteristic incident radiation. For example, a standard tungsten (target) X-ray generator will produce an excited K-alpha line at approximately 59.3 keV (0.21 Angstrom). Therefore, the signal-to-noise ratio may be improved by discriminating and identifying any resultant K-alpha caustic from other caustics produced at different characteristic lines and/or the Bremsstrahlung (continuous background radiation from the X-ray target). This consideration can also be extended to the incoherent signal contributions produced by Compton scatter.

Figure 20:
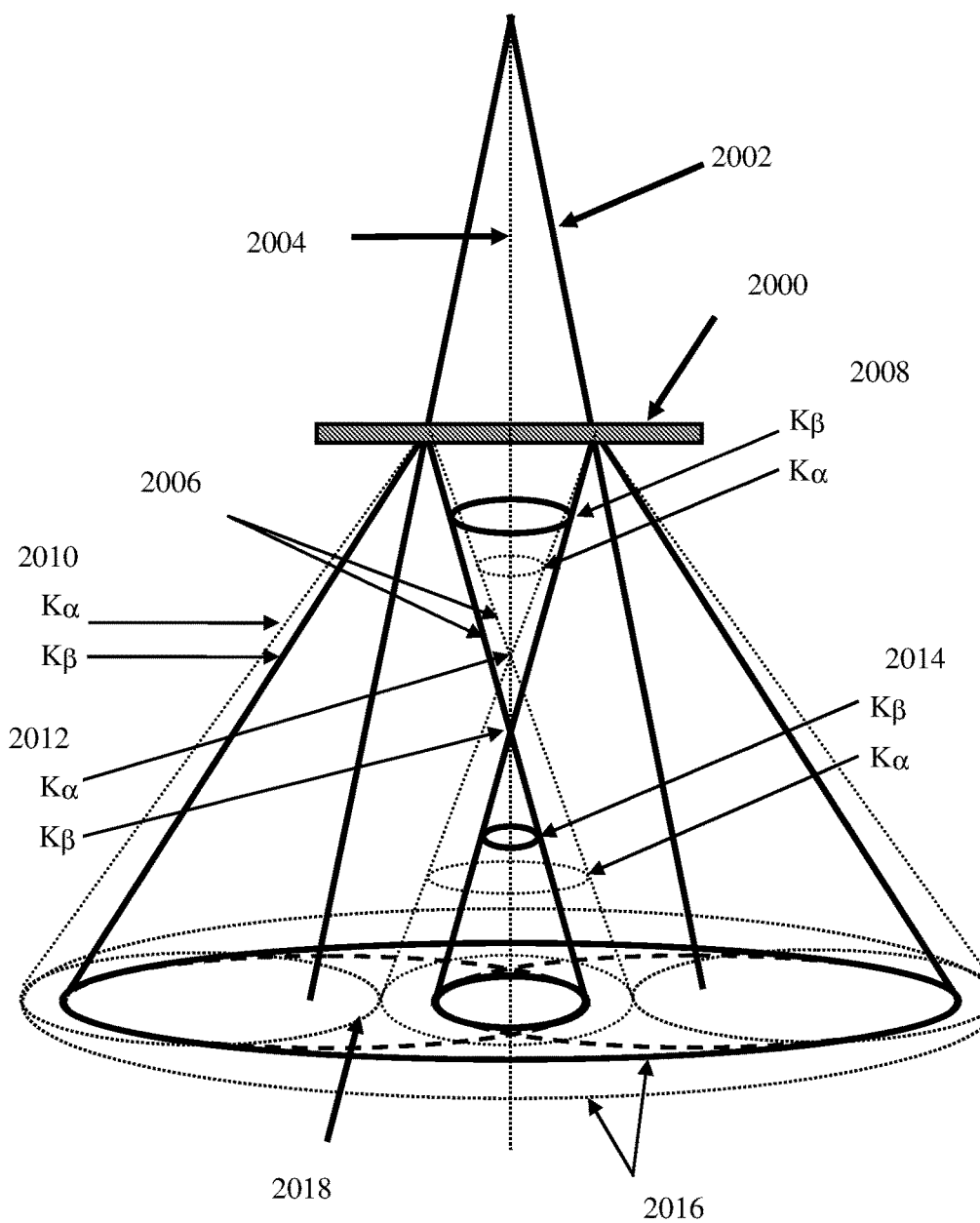
FIG. 20 shows an energy resolving scatter gathering apparatus.

FIG. 20 illustrates an embodiment that utilises an energy resolving technique. Two sets of Debye cones are illustrated for representative Kα and Kβ transitions from the sample 2000, which are generated by tubular primary beam 2002 of electromagnetic radiation (X-ray in this example) centred about a primary axis 2004. All wavelengths in the spectrum that satisfy Bragg's condition would produce Debye cones at different two theta angles (i.e. half opening angle of the cone). Thus multiple caustic patterns are formed in parallel. However, given sufficient resolution a detector could be employed to detect and identify all such different caustics. In the diagram, the solid lines represent features associated with the representative Kβ transition while the dashed lines represent features associated with the representative Kα transition. In a similar manner as described above and as illustrated at 2006, a continuum of Kα and Kβ Debye cones around a circular path forms a relatively high intensity convergent tubular beam. The diagram also shows Debye cones 2010, closing rims 2008, hotspots 2012 and opening rims 2014. Reference 2018 illustrates one Kα Debye ring in a continuum of Debye rings around a circular path recorded by a planar sensor normal to the primary axis. The outer rims 2016 (for Kα and Kβ cones) are recorded by a planar sensor normal to the primary axis.

Approximate Kα and Kβ values for selected elements are as follows:

| Element | $K_\alpha$ (approx. keV) | $K_\beta$ (approx. keV) |
|---|---|---|
| Silver Ag (47) | 22 | 25 |
| Terbium Tb (65) | 44 | 50 |
| Tungsten W (74) | 59 | 67 |
| Platinum Pt (78) | 67 | 76 |

The use of energy resolved techniques, optionally together with monochromising the source, can help reduce noise produced by background incoherent signals generated by Compton scattering that might in some cases otherwise swamp the coherent signal. The Compton scattering can also be measured in order to aid analysis.

Various improvements and modifications can be made to the above without departing from the scope of the disclosure.

The invention claimed is:

1. A method of sample analysis, comprising:
emitting, from a radiation source, a primary interrogating beam of electromagnetic radiation that includes at least one tubular beam having a shape which comprises a right circular cylinder or a cone;
irradiating a sample with the primary interrogating beam, wherein the primary interrogating beam is configured to interact with the sample to thereby cause cones of diffracted radiation to be emitted from the sample, the cones providing rings in an image plane, and wherein an overlap of a continuum of the rings is configured to form one or more caustic rims; and
collecting diffracted radiation with a detector at the image plane by adjusting relative arrangements of two or more of the radiation source, the sample, and the detector between successive measurement positions in order to scan the sample in the image plane to collect multiple images at different image plane positions and to obtain successive images at successive angular positions around a caustic rim, such that each point around the caustic rim has a different perspective view of the sample, and caustic rim data from different positions in the image plane are combined to form composite perspective views of the sample.

2. The method of claim 1, wherein an image of the sample is formed by combining a plurality of the composite perspective views of the sample corresponding to different positions along a radial direction measured from the centre point of the path defined by the primary interrogating beam.

3. The method of claim 1, wherein the tubular beam is formed by a collimator provided with said radiation source that comprises an electromagnetic radiation blocking body portion and one or more electromagnetic radiation transmitting apertures, the shape of which defines the shape of the at least one tubular beam.

4. The method of claim 1, wherein:
a composite image is formed by a combination of composite perspective views which produce a focal plane image convolved with an apparent annular aperture having a zero effective aperture at a rim; and
the combination of composite perspective views provides z height information for the focal plane image to enable two theta diffraction angles to be calculated automatically.

5. The method of claim 4, wherein a spatial origin of one or more diffraction peaks corresponding to focal plane features of the sample in the image plane is used to identify material properties.

6. The method of claim 1, wherein spatial information is established via a movie sequence formed by a display of successive composite perspective views and by showing image features being translated around a circular path as a function of their relative position with respect to a convergence or datum plane.

7. The method of claim 1, wherein:
spatial information is established via rotation of the sample under inspection, arranged to conserve the direction of parallax along one axis; and
a binocular stereoscopic image sequence having a left perspective view sequence and a right perspective view sequence is displayed on a visual display having horizontal display axes by maintaining the direction of parallax in the visual display along the horizontal display axes but in opposite directions for the left perspective view sequence and the right perspective view sequence.

8. The method of claim 1, wherein spatial information is established via a sequence or stack of focal plane images, produced by a combination of composite perspective views being displayed as a movie formed by sequential images along a z-axis.

9. The method of claim 1, comprising solving for a sample diffraction angle for a known relative position with respect to an associated rim, measured parallax, and separation between rays of the primary interrogating beam for two different radial directions.

10. The method of claim 1, wherein:
depth information is identified along radial paths that are independent of a scattering angle of the cones of diffracted radiation to be emitted from the sample; and
tomography or laminography is carried out on the basis of said identified depth information.

11. The method of claim 1, wherein images of extended objects directly attributable to individual rays of the primary interrogating beam are produced and combined with images of extended objects directly attributable to other individual rays of the primary interrogating beam to provide material identification and/or characterisation.

12. The method of claim 11, wherein said material identification and/or characterisation comprises one of accounting for a sample's preferred orientation, and accounting for a sample's grain size.

13. The method of claim 1, wherein captured perspective images are relayed in a movie sequence formed by a sequence of perspective images, which exhibit rotating features, in planes parallel to a sensor surface, as a function of their relative depth (Z axis) in a visual display.

14. The method of claim 1, wherein perspective images produced at different scattering angles are mapped together to provide colour encoding implemented via a corresponding pixel positions input to a lookup table.

15. The method of claim 1, comprising:
irradiating the sample with broadband or white electromagnetic radiation; and
performing the sampling at different energy resolutions, wherein the electromagnetic radiation comprises K-alpha and/or K-beta characteristic radiation.

16. A sample analysis apparatus, comprising:
an electromagnetic radiation source arranged to emit a primary interrogating beam of electromagnetic radiation that includes at least one tubular beam having a shape which comprises a right circular cylinder or a cone, said primary interrogating beam being suitable for irradiating a sample, wherein the primary interrogating beam is configured to interact with the sample to thereby cause cones of diffracted radiation to be emitted from the sample, said cones providing rings in an image plane, and wherein an overlap of a continuum of said rings is configured to form one or more caustic rims;
a detector configured to collect diffracted electromagnetic radiation at the image plane; and
a processor for sampling said diffracted electromagnetic radiation,
wherein the apparatus is configured to adjust relative arrangements of two or more of the source, the sample, and the detector between successive measurement positions in order to scan the sample in the image plane, to collect multiple images at different image plane positions, and to obtain successive images at successive angular positions around a caustic rim, such that each point around the caustic rim has a different perspective view of the sample, and caustic rim data from different positions in the image plane are combined to form composite perspective views of the sample.

17. A non-transitory computer program product for use with a sample analysis apparatus that comprises an electromagnetic radiation source arranged to emit a primary interrogating beam of electromagnetic radiation that includes at least one tubular beam having a shape which comprises a right circular cylinder or a cone, said primary interrogating beam being suitable for irradiating a sample, wherein the primary interrogating beam is configured to interact with the sample to thereby cause cones of diffracted radiation to be emitted from the sample, said cones providing rings in an image plane, and wherein an overlap of a continuum of said rings is configured to form one or more caustic rims, a detector configured to detect diffracted electromagnetic radiation at the image plane; and a processor for sampling said diffracted electromagnetic radiation, said non-transitory computer program product comprising instructions that, when executed by the processor, enable the apparatus to control an adjustment of relative arrangements of two or more of the source, the sample, and the detector between successive measurement positions in order to scan the sample in the image plane to collect multiple images at different image plane positions, and to obtain successive images at successive angular positions around a caustic rim, such that each point around the caustic rim has a different perspective view of the sample, and caustic rim data from different positions in the image plane are combined to form composite perspective views of the sample.

* * * * *